(12) United States Patent
Busa et al.

(10) Patent No.: US 10,823,746 B1
(45) Date of Patent: Nov. 3, 2020

(54) LATERAL FLOW IMMUNOASSAY TEST READER AND METHOD OF USE

(71) Applicants: William Busa, Bahama, NC (US); Phillip H. Coelho, Sacramento, CA (US); Paul Getchel, El Dorado Hills, CA (US)

(72) Inventors: William Busa, Bahama, NC (US); Phillip H. Coelho, Sacramento, CA (US); Paul Getchel, El Dorado Hills, CA (US)

(73) Assignee: Thermogenesis Holdings, Inc., Rancho Cordova, CA (US)

( * ) Notice: Subject to any disclaimer, the term of this patent is extended or adjusted under 35 U.S.C. 154(b) by 0 days.

(21) Appl. No.: 16/885,436

(22) Filed: May 28, 2020

Related U.S. Application Data

(60) Provisional application No. 63/029,003, filed on May 22, 2020.

(51) Int. Cl.
*G01N 35/00* (2006.01)
*G01N 33/569* (2006.01)
(Continued)

(52) U.S. Cl.
CPC ....... *G01N 35/00029* (2013.01); *G01N 21/78* (2013.01); *G01N 33/56983* (2013.01);
(Continued)

(58) Field of Classification Search
CPC ............. G01N 35/00029; G01N 21/78; G01N 33/56983; G01N 35/00871;
(Continued)

(56) References Cited

U.S. PATENT DOCUMENTS

| 10,295,472 B2 | 5/2019 | Xie et al. |
| 2003/0068665 A1 | 4/2003 | Kawamura et al. |
| (Continued) | | |

FOREIGN PATENT DOCUMENTS

CN        111337669    *   6/2020

OTHER PUBLICATIONS

Koczula, K. et al. "Lateral Flow Assays" Essays in Biochemistry (2016) vol. 60, pp. 111-120.
(Continued)

*Primary Examiner* — Jill A Warden
*Assistant Examiner* — Jacqueline Brazin
(74) *Attorney, Agent, or Firm* — McDonnell Boehnen Hulbert & Berghoff LLP

(57) ABSTRACT

A reader for a lateral flow test device includes a tray or drawer, extendable from the reader, which receives the test device. The tray includes a calibration test pattern affixed or printed thereon placed proximate to the test device and in alignment with the axis of the test device. As the tray is closed and the test device is inserted to the reader, the calibration test pattern is first read by an optics unit including a photodiode. The resulting photodiode output provides a calibration curve S that the reader then uses to correct for any non-linear response of the reader's optical or electronic systems, thus insuring that every reader will yield the same readout for a given test cartridge, despite reader-to-reader variations or reader degradation with time. One use of the reader is for detection of SARS-CoV-2 infection.

8 Claims, 31 Drawing Sheets

(51) Int. Cl.
*G01N 21/78* (2006.01)
*G01S 19/01* (2010.01)

(52) U.S. Cl.
CPC ........ *G01N 35/00871* (2013.01); *G01S 19/01* (2013.01); *G01N 2035/00108* (2013.01); *G01N 2035/00891* (2013.01); *G01N 2201/06113* (2013.01); *G01N 2333/165* (2013.01)

(58) Field of Classification Search
CPC .......... G01N 2035/00108; G01N 2035/00891; G01N 2201/06113; G01N 2333/165; G01S 19/01
USPC ......................................................... 422/404
See application file for complete search history.

(56) References Cited

U.S. PATENT DOCUMENTS

| | | | | |
|---|---|---|---|---|
| 2004/0050143 | A1* | 3/2004 | Hoagland | G01N 31/10 73/31.05 |
| 2005/0037338 | A1* | 2/2005 | Tseng | C12Q 1/701 435/5 |
| 2006/0040406 | A1* | 2/2006 | Schneider | G16H 40/20 436/514 |
| 2006/0210435 | A1* | 9/2006 | Alavie | G01N 21/253 422/65 |
| 2006/0240541 | A1 | 10/2006 | Petruno et al. | |
| 2007/0188736 | A1 | 8/2007 | Fouquet et al. | |
| 2009/0155921 | A1* | 6/2009 | Lu | G01N 21/274 436/164 |
| 2010/0323343 | A1* | 12/2010 | Egan | C12Q 1/6804 435/5 |
| 2011/0275162 | A1* | 11/2011 | Xie | G01N 21/78 436/164 |
| 2013/0273528 | A1* | 10/2013 | Ehrenkranz | G01N 21/8483 435/6.1 |
| 2016/0238601 | A1* | 8/2016 | Baric | C07K 14/005 |
| 2016/0290912 | A1* | 10/2016 | Kent | G01N 15/1475 |
| 2020/0001299 | A1 | 1/2020 | Fleming et al. | |
| 2020/0241010 | A1* | 7/2020 | Skraba | A61B 10/0045 |

OTHER PUBLICATIONS

Pilavaki, E. et al. "Optimized Lateral Flow Immunoassay Reader for the Detection of Infectious Diseases in Developing Countries" Sensors (2017) vol. 17, 11 pages.

Yang, Y. et al. "Development of a Quantifiable Optical Reader for Lateral Flow Immunoassay" proceedings of the 8th International Conference on Biomedical Engineering and Informatics (BME)(2015) p. 344-349.

Thermogenesis, COVID-19 test kit, https://thermogenesis.com/covid-19-test-kit/.

* cited by examiner

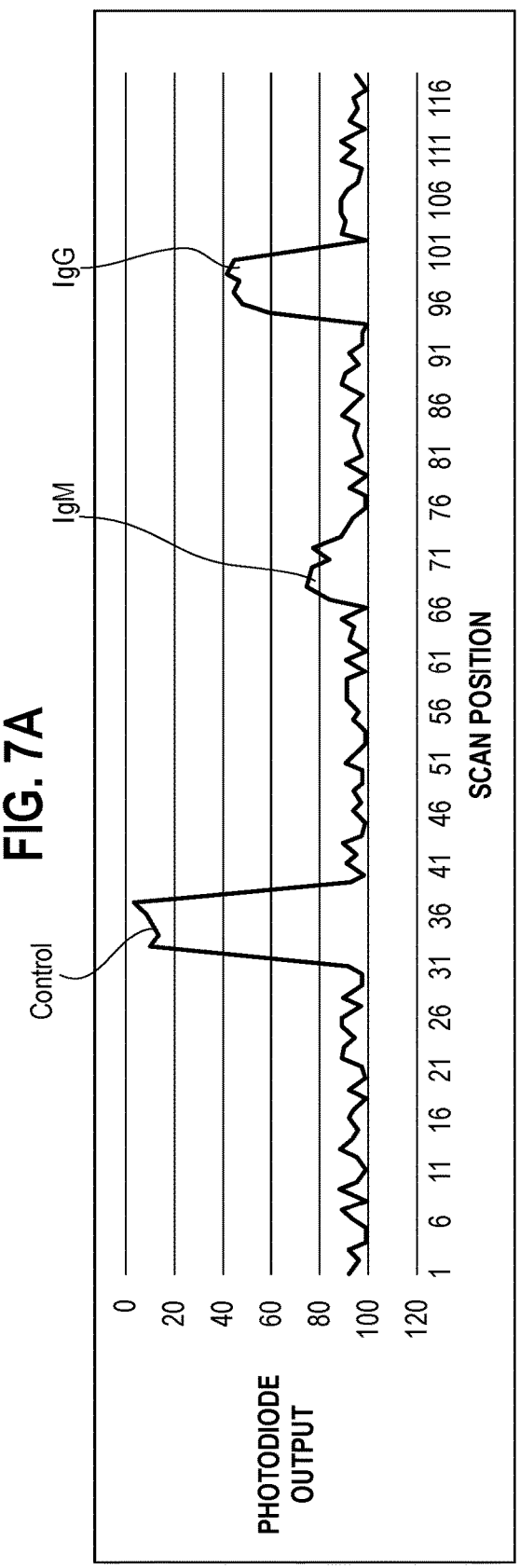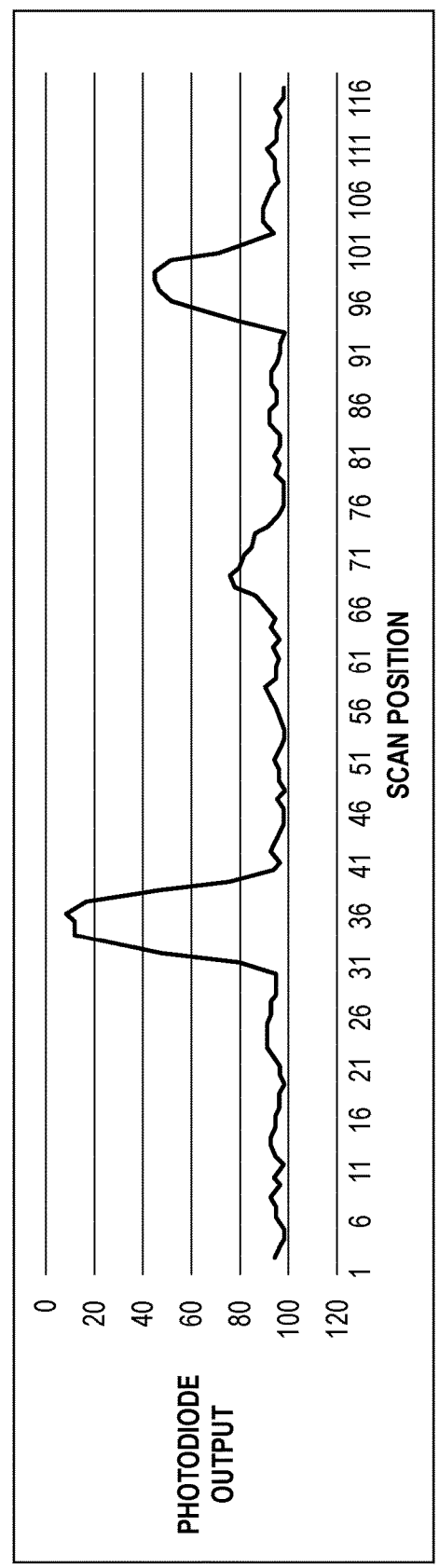

FIG. 41

```
subject_id, read_date, read_time_utc, reader_latitude, reader_longitude, reader_id, test_batch_no, igm_absorbance, igg_absorbance, ctrl_absorbance, igm_ratio, igg_ratio, igm_result, igg_result, error_code
AE3200459, 2020-06-17, 13:33:50, 36.16819, -78.87204, TG00305, SY2020-357, 0.03412, 0.07724, 0.10049, 0.33954, 0.76863, WEAKPOS, STRONGPOS, [NULL]
AE3200460, 2020-06-17, 13:48:12, 36.16819, -78.87204, TG00305, SY2020-357, 0.01945, 0.0371, 0.12994, 0.14968, 0.28552, WEAKPOS, WEAKPOS, [NULL]
AE3200461, 2020-06-17, 13:53:49, 36.16819, -78.87204, TG00305, SY2020-357, 0.00359, 0.09595, 0.12043, 0.02981, 0.79673, NEG, STRONGPOS, [NULL]
AE3200462, 2020-06-17, 14:05:07, 36.16819, -78.87204, TG00305, SY2020-357, [NULL], 0.10204, 0.11549, [NULL], 0.88354, NEG, STRONGPOS, [NULL]
AE3200463, 2020-06-17, 14:11:53, 36.16819, -78.87204, TG00305, SY2020-357, [NULL], [NULL], 0.12133, [NULL], [NULL], NEG, NEG, [NULL]
AE3200464, 2020-06-17, 15:44:20, 36.16819, -78.87204, TG00305, SY2020-357, 0.08295, 0.02047, 0.12134, 0.66712, 0.16463, STRONGPOS, NEG, [NULL]
AE3200465, 2020-06-18, 7:35:15, 36.16819, -78.87204, TG00305, SY2020-339, [NULL], [NULL], [NULL], [NULL], [NULL], [NULL], [NULL], 6
AE3200466, 2020-06-18, 7:42:48, 36.16819, -78.87204, TG00305, SY2020-357, [NULL], [NULL], 0.10977, [NULL], [NULL], NEG, NEG, [NULL]
AE3200467, 2020-06-18, 8:04:27, 36.16819, -78.87204, TG00305, SY2020-357, 0.03555, 0.01047, 0.1194, 0.29774, 0.08769, WEAKPOS, NEG, [NULL]
AE3200468, 2020-06-18, 8:16:59, 36.16819, -78.87204, TG00305, SY2020-357, [NULL], 0.12403, 0.11337, [NULL], 1.09403, [NULL], STRONGPOS, [NULL]
```

FIG. 42

| subject_id | read_date | read time_utc | read latitude | reader longitude | reader_id | test_batch_no | igm absorbance | igg absorbance | ctrl absorbance | igm_ratio | igg_ratio | igm_result | igg_result | error code |
|---|---|---|---|---|---|---|---|---|---|---|---|---|---|---|
| AE3200459 | 2020-06-17 | 13:33:50 | 36.16819 | -78.87204 | TG00305 | SY2020-357 | 0.03412 | 0.07724 | 0.10049 | 0.33954 | 0.76863 | WEAK POS | STRONG POS | [NULL] |
| AE3200460 | 2020-06-17 | 13:48:12 | 36.16819 | -78.87204 | TG00305 | SY2020-357 | 0.01945 | 0.0371 | 0.12994 | 0.14968 | 0.28552 | WEAK POS | WEAK POS | [NULL] |
| AE3200461 | 2020-06-17 | 13:53:49 | 36.16819 | -78.87204 | TG00305 | SY2020-357 | 0.00359 | 0.09595 | 0.12043 | 0.02981 | 0.79673 | NEG | STRONG POS | [NULL] |
| AE3200462 | 2020-06-17 | 14:05:07 | 36.16819 | -78.87204 | TG00305 | SY2020-357 | [NULL] | 0.07725 | 0.11549 | [NULL] | 0.88354 | NEG | STRONG POS | [NULL] |
| AE3200463 | 2020-06-17 | 14:11:53 | 36.16819 | -78.87204 | TG00305 | SY2020-357 | [NULL] | [NULL] | 0.12133 | [NULL] | [NULL] | NEG | NEG | [NULL] |
| AE3200464 | 2020-06-17 | 15:44:20 | 36.16819 | -78.87204 | TG00305 | SY2020-357 | 0.8295 | 0.02047 | 0.12434 | 0.66712 | 0.16463 | STRONG POS | NEG | [NULL] |
| AE3200465 | 2020-06-18 | 7:35:15 | 36.16819 | -78.87204 | TG00305 | SY2020-359 | [NULL] | [NULL] | [NULL] | [NULL] | [NULL] | [NULL] | [NULL] | 6 |
| AE3200465 | 2020-06-18 | 7:42:48 | 36.16819 | -78.87204 | TG00305 | SY2020-357 | [NULL] | [NULL] | 0.10977 | [NULL] | [NULL] | NEG | NEG | [NULL] |
| AE3200467 | 2020-06-18 | 8:04:27 | 36.16819 | -78.87204 | TG00305 | SY2020-357 | 0.03555 | 0.01047 | 0.1194 | 0.29774 | 0.08769 | WEAK POS | NEG | [NULL] |
| AE3200468 | 2020-06-18 | 8:16:59 | 36.16819 | -78.87204 | TG00305 | SY2020-357 | [NULL] | 0.12403 | 0.11337 | [NULL] | 1.09403 | [NULL] | STRONG POS | [NULL] |

LATERAL FLOW IMMUNOASSAY TEST READER AND METHOD OF USE

PRIORITY

This application claims priority to U.S. Provisional application Ser. No. 63/029,003 filed on May 22, 2020, the content of which is incorporated by reference herein, including the appendix thereof.

FIELD

This disclosure relates to the field of readers for lateral flow immunoassay test devices. Such test devices typically take the form factor of a test strip or cartridge.

BACKGROUND

Lateral flow immunoassay (LFA) devices are a paper or nitrocellulose-based platform for the detection and optional quantitation of analytes, in complex mixtures (e.g. biological fluids such as blood or saliva). The sample is placed in a sample well of the test device, and the results are obtained in typically 3-30 minutes. Such test devices can exist as standalone devices, in which is the device is read by the unaided eye. Such test devices may also be used in conjunction with a dedicated reader. The reader includes optical components, e.g., imager or photodiode array, for assessing the test strip and a processing unit generating a result, e.g., "positive", "negative" or the like. LFA test devices are used in a variety of testing scenarios, including pregnancy detection, detection of antigens indicating infection by a virus, detection of biomarkers of disease, metabolites, and other molecular targets, as well as screening for animal diseases, chemicals, toxins, and water pollutants, among others.

Background information on lateral flow assays and related chemistry is found in the review article of K. Koczula et al., *Lateral Flow Assays*, Essays in Biochemistry (2016) v 0.60 p. 111-120, the content of which is incorporated by reference herein. Dedicated readers for lateral flow immunoassay devices are disclosed in E. Pilavaki et al., *Optimized Lateral Flow Immunoassay Reader for the Detection of Infectious Diseases in Developing Countries*, Sensors vol. 17, 2673 (2017); Y. Yang et al., *Development of a Quantifiable Optical Reader for Lateral Flow Immunoassay*, proceedings of the 8th International Conference on Biomedical Engineering and Informatics (BME)(2015) p. 344-349; Xie et al., U.S. Pat. No. 10,295,472; Lu et al., US patent application publication 2009/0155921 and Fleming et al., US patent application publication 2020/0001299.

By way of example and not limitation, and as is explained in the Koczula et a. article, and with reference to FIGS. 1 and 2A-2B of the appended drawings, the principle behind a typical configuration of a LFA is simple: a liquid sample (or its extract, e.g., blood, sweat, urine, saliva etc.) containing the analyte of interest is introduced into a sample well of a test device (e.g., the test strip 10). The liquid sample progresses via capillary action through various zones (typically narrow lines oriented perpendicular to the long axis of the strip), on which molecules that can interact with the analyte are attached. A typical lateral flow test strip 10 consists of overlapping membranes that are mounted on a backing card for better stability and handling. As shown in FIG. 2A, the liquid sample is applied at one end of the strip 10, on the absorbent sample pad, which is impregnated with buffer salts and surfactants that make the sample suitable for interaction with the detection system. The sample pad ensures that the analyte present in the sample will be capable of binding to the capture reagents of conjugates and on the membrane. The treated sample migrates through the conjugate release pad, which contains antibodies that are specific to the target analyte and are conjugated to colored or fluorescent particles—most commonly colloidal gold and latex microspheres.

The sample, together with the conjugated antibody bound to the target analyte, migrates along the strip 10 into the detection zone. The detection zone consists of a porous membrane (usually composed of nitrocellulose) with specific biological components (mostly antibodies or antigens) immobilized in lines oriented perpendicular to the long axis of the test strip. Their role is to react with the analyte bound to the conjugated antibody (Ab). Recognition of the sample analyte results in an appropriate response on the test line, while a response on a control line indicates the proper liquid flow through the strip. The read-out, represented by the lines appearing with different intensities (see FIG. 2B), can be assessed by naked eye or alternatively using a dedicated reader, e.g., one of the readers in the above-cited references. In order to test multiple analytes simultaneously under the same conditions, additional test lines of antibodies specific to different analytes can be immobilized in an array format. The liquid flows across the device because of the capillary force of the strip material and, to maintain this movement, an absorbent pad is attached at the end of the strip. The role of the absorbent pad is to wick the excess reagents and prevent backflow of the liquid.

While FIGS. 1 and 2A show the test device in the form of a strip 10, it is also known to incorporate the strip 10 into a cartridge-type device as shown in FIG. 2 of U.S. '472 patent cited above or the Lu et al. patent application publication, FIG. 7 thereof.

The present reader and related methods of this disclosure are designed to be used in conjunction with a test device in the form factor of a cartridge containing a test strip; however the teachings below can be adapted to a test strip format per se, such as shown in FIGS. 1 and 2 of this document and thus the present disclosure is intended to cover both types of test devices.

Additionally, while the present disclosure is capable of being used in conjunction with any of the currently known purposes of lateral flow immunoassays (as explained above in the previously cited patents and technical literature, such descriptions of which are incorporated by reference), one particular application of the present disclosure is a reader for a lateral flow immunoassay test device configured for detection of Immunoglobulin M (IgM) and Immunoglobulin G (IgG) antibodies in human serum, whole blood or plasma from individuals suspected of infection with the SARS-CoV-2 virus, which causes a disease referred to as COVID-19. SARS-CoV-2 is the name assigned to the novel coronavirus currently causing a worldwide pandemic.

SUMMARY

In a first aspect of this disclosure, a reader is provided for a lateral flow test device having an axis and one or more test lines and a control line oriented perpendicular to the axis. The reader includes a housing enclosing electronics and an optics unit configured for reading the one or more test lines and the control line of the test device. The reader further includes a tray extendable from the housing between a closed position and an open position. The tray is adapted to receive the test device when the tray is extended to the open position, and when the test device is placed in the tray and the tray moved to a closed position the one or more test lines and control line are read by the optics unit. The tray further includes an upper surface, the upper surface provided with an optical calibration test pattern spaced from the test device and positioned in alignment with the axis of the test device. The test pattern facilitates performance of a self-test of the optics unit upon movement of the tray from the open position to the closed position and immediately before the test device is read.

In one possible format, the calibration test pattern is in the form of a linear series of bands of known, graded optical intensities, each of the bands oriented perpendicular to the axis of the test device. For example there may be at least five or at least ten bands of known graded optical intensities. In one possible configuration, the calibration test pattern is printed on a material and the material is placed in a designated location on the upper surface of the tray.

In one embodiment, the optics unit includes a diode laser generating a light output, a line generator converting the light output of the diode laser to a line format, and a photodiode reading the intensity of the laser light reflected from the test device. The line format of the laser light is oriented perpendicular to the axis of the test device and in the same orientation of each of the bands of the calibration optical test pattern.

The reader may include several features, such as a rechargeable battery and a port receiving a recharging cable for recharging the battery, and RFID reader, and/or a wireless transmitter transmitting results of a reading operation to a remote computing device.

In one possible configuration the test device is in the form of a test strip. Alternatively, the test device can take the form of a cartridge containing a test strip.

In one possible use, the test device includes a test strip configured to test for presence of antibodies to the SARS-CoV-2 virus. A testing system is disclosed including the test device configured to test for presence of antibodies to the SARS-CoV-2 virus and the reader of this disclosure.

In another aspect, a method is provided for reading a lateral flow test device having one or more test lines and a control line with a reader having an electro-optical system (electronics and an optics unit). The reader includes a tray extendable from the reader from an open position in which the test device is placed in the tray to a closed position whereby the test device is read. The method includes the steps of: reading a calibration test pattern placed on the tray with the optics unit of the reader, the optics unit including a photodiode; performing a self-test of the reader's electro-optical system, wherein the self-test includes generating a calibration curve S characterizing any non-linear response of the components of the electro-optical system; and reading the test and control lines of the test device with the optics unit, including using the calibration curve S to convert photodiode output values to % absorbance values.

In another aspect, a method is provided for calibrating a reader for a lateral flow test device. The reader includes an optics unit including a photodiode receiving light reflected from a test strip provided with the test device. The method includes steps of: a) scanning in the reader a calibration test pattern; b) acquiring photodiode output values during the scanning step a); c) optionally inverting the output values; d) calculating average peak heights Ai in the output values; e) storing the results of step d) as an array of peak heights and linear position data [Ai, Pi], the linear position data Pi indicative of incremental linear positions at which the calibration test pattern was scanned in step a); and f) fitting a spline curve S to the array data and saving the equations for the spline curve S, wherein the spine curve S characterizes any non-linear response of the optics system or associated electronics.

In the above method, in one configuration the scanning step a) comprises manual insertion of a tray carrying the test device into the reader, and wherein the tray includes the calibration test pattern. The test device includes a test strip configured to test for presence of antibodies to the SARS-CoV-2 virus.

In still another aspect, a method of reading a lateral flow test device with a reader is disclosed. The reader including an optics unit including a photodiode receiving light reflected from a test strip provided with the test device. The method includes the steps of: a) scanning with the reader the test strip; b) acquiring photodiode output values during the scanning step a); c) optionally inverting the output values; d) converting the photodiode output values to % absorbance values using equations for a spline curve S, wherein the spine curve S characterizes any non-linear response of the optics system, and wherein spline curve S is generated during calibration of the optics unit prior to scanning step a); e) identifying peaks in normalized absorbance data; f) assigning labels to the peaks identified in step e); g) applying local baseline corrections and calculating peak areas for each of the labeled peaks of step f); and h) calculating ratios of peak areas associated with test lines of the test device to a control line of the test device.

In still another aspect, a tray is provided for holding a lateral flow test device and configured for movement between open and inserted positions relative to a reader for reading the test device, the reader further including a ratchet pawl and a spring. The tray includes a surface having features for receiving and holding the test device; a set of ratchet teeth formed on the tray, wherein the pawl and spring of the reader are positioned so as to bias the pawl into engagement with the ratchet teeth; the tray further includes a first feature disengaging the pawl from the set of ratchet teeth upon complete insertion of the tray into the reader and enabling the tray to be withdrawn from the reader; wherein when the tray is in intermediate positions between the open and inserted position the pawl, spring and ratchet teeth prevent retraction of the tray from the reader.

In another possible configuration, QR codes are placed on the bottom surface of the cartridge which are read by an accessory device on which the reader sits. The accessory device provides a means for moving the tray in and out with the aid of a threaded rod in a programmed fashion. This configuration allows for reading the elapsed time for emergence of a positive result on the test strip, which can provide further information useful in assessing the state of the sample and therefore result generated by the reader.

Accordingly, in one further aspect, an accessory unit to lateral flow assay reader having a moveable tray holding a test device is disclosed. The tray is moveable from open and closed positions. The accessory unit includes a structure holding the reader and an electro-mechanical system engaging the tray and moving the tray and test device into the reader between the open and closed positions in a programmed manner, such that the test device is positioned proximate to the optics unit, such that at least one of the one or more test lines is read repeatedly for a period of time by the optics unit, whereby the reader is able to record, either directly or indirectly, changes in the color intensity of the one or more test lines over time.

BRIEF DESCRIPTION OF THE DRAWINGS

FIG. 7A is an example of a plot of the photodiode output as a function of scan position for a given test device.

FIG. 7B is an example of the plot of FIG. 7A after signal correction process has been performed.

In FIGS. 33, 34, 37 and 38 the housing or "skin" for the accessory unit is shown in broken lines in order to show the electro-mechanical system and its operation in better detail.

FIG. 41 is an illustration of a portion of a CSV file including identification data and test result data generated in the reader and transmitted wirelessly to a remote computing device, e.g., smartphone.

FIG. 42 is an illustration of a portion of a spreadsheet or spreadsheet which aggregates anonymized CSV files, such as the type shown in FIG. 41, and arranges them in a format for data mining, generation of reports, and other uses.

DETAILED DESCRIPTION

Overview

Figure 1:
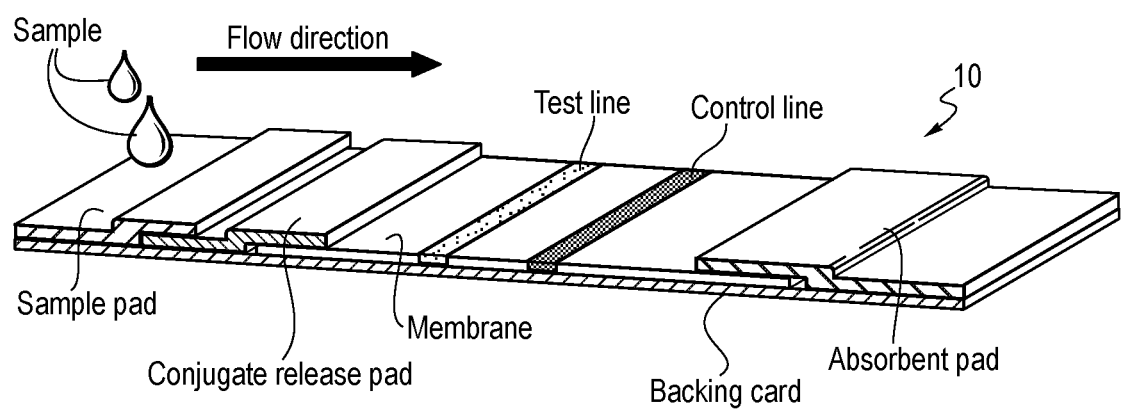
FIG. 1 is a perspective view of a typical configuration of a lateral flow immunoassay (LFA) test strip. The test strip is usually composed of the following elements: sample pad, conjugate release pad, membrane with immobilized antibodies and an adsorbent pad. The components of the strip are usually fixed to an inert backing material

As noted above, today's lateral flow immunoassays (LFAs) are notoriously challenging for untrained users to properly read directly by eye, especially when either manufacturing variances or the biological variability common among patients leads to weakly stained test bands, posing a possibility of incorrect reads. Such scenarios can cause the user to generate either false-negative or false-positive test results. Incorrect reads (and the false results they can generate) not only reflect badly on the product, but can create a public health hazard. Additionally, in the large-scale screening environment (such as employer-sponsored screens of employees), by-hand record keeping slows test administration workflow and introduces the very real potential for recordkeeping errors.

The reader of this disclosure is designed to replace direct reading of a test device by eye with a more accurate and automated reading done by machine, i.e., the reader of this disclosure. The reader can be configured to employ features expected to be particularly important to employers, who are managing the safe return of employees in the current COVID-19 epidemic, and for FDA approved home use. A number of features and benefits of the reader are described at the end of this document. Such advantages and benefits will be more completely appreciated after consideration of the many mechanical, optical, electrical and software aspects that are incorporated in the design and described in the following discussion with reference to FIG. 3 et seq.

In the following discussion, and with reference to FIGS. 3 and 3A, we will discuss for purposes of illustration and not limitation a test device 20 having a test strip 110, the device 20 in the form of a cartridge having a well 22 for introduction of the liquid sample and an opening 24 revealing a control line 26 and two test lines 28 (such as IgG and IgM lines) found on a test strip within the cartridge. The test device 20 is designed for insertion into a reader shown at 30, which includes a tray 32 or drawer that slides out from the reader 30 and has features for placement of the test device 20 into the tray and subsequent insertion into the reader for reading. The top of the reader 30 has a display 34 configured to display results from the read operation, as will be described in detail below. The reader 30 may also include a text panel 36 for printed instructions on use or explanations for interpretation of the test results. The reader 30 has a rechargeable battery and designed to be held in the hand of a user.

Figure 3:
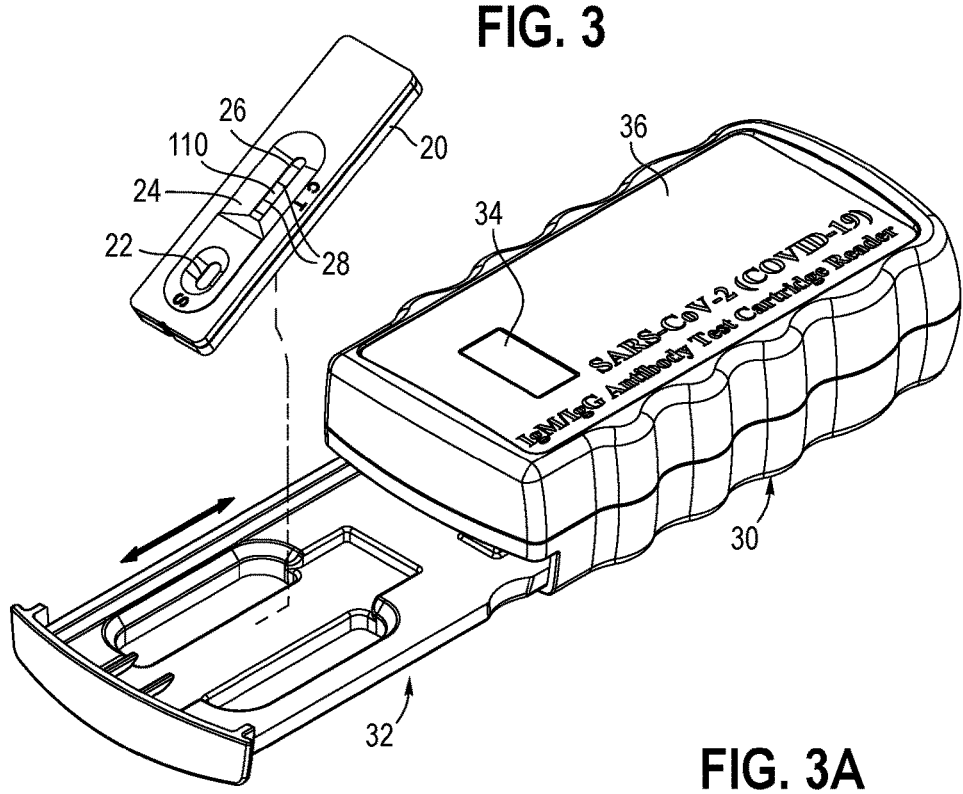
FIG. 3 is a perspective view of a test device and optical reader of this disclosure.
Figure 4:
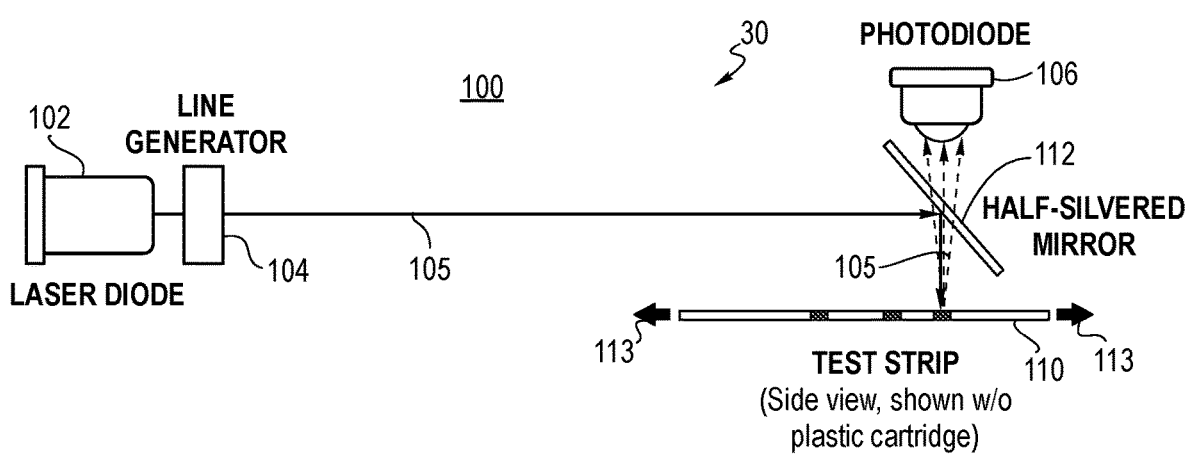
FIG. 4 is a more detailed schematic view of the optics of the reader of FIG. 3.

As an overview, and with reference to FIG. 4, the core of the reader 30 itself is a simple yet precise optical system 100 employing inexpensive optical components: a low-power green diode laser 102 (the light source), a line-generator 104 which functions to convert the laser's Gaussian dot-like output into a line format 105 of laser light, and a photodiode 106, to read the intensity of the laser light reflected from the test strip 110 contained within the cartridge 20 of FIG. 3. The photodiode in one embodiment has peak response for incident wavelength of 525 nm, which is at or close to the wavelength of light emitted by the laser. The line generator 104 may take the form of a lens or combination of a lens and slits, masks, and/or baffles shaping and converting the light output into a line. The design further includes a half silvered mirror or beam splitter 112 which directs the incident line of laser light on the test strip and allows the reflected light to pass through the mirror 112 and fall on the photodiode 106. The aperture or field of view of the photodiode is preferably large enough so as to encompass the ray bundle reflected from the test strip 110, e.g., 4 mm in diameter.

The laser line 105, projected onto the test strip as a line parallel to the cartridge's test and control lines (see FIG. 5), is very narrow (e.g., about 48 μm wide), permitting high-resolution reads (enabling discrimination of lines from stains) without an expensive camera and lenses, plus the ability to perform boxcar averaging of the scan, e.g., to optimize the optical system's signal-to-noise (S/N) ratio, for the best possible sensitivity and dynamic range.

Scanning the laser line along the length of the test strip is accomplished by the manual motion of inserting a tray 32 (FIG. 3) carrying the test device 20 into the reader 30 by the user (or optionally by withdrawal of the tray carrying the test device from the reader, or during insertion and withdrawal), as indicated by the arrows 113 (FIG. 4), thus enabling a reader with no powered moving parts. For example, in one possible configuration, the reader does not require the use of a motorized stage or other mechanical system to move the optics or test strip relative to each other in a read operation. The reader may include a separate system, such as an optical system in the form of LEDS and one or more photodiodes, to determine the position of the cartridge and test strip within the reader during read operations, which will be described later.

When the reader is not in use, the optical components are in an OFF state and the compartment containing the optical components is closed from the environment by the tray 32 (FIG. 3) when it is in a closed or stowed position, thereby protecting the optical components from dust, dirt, and moisture. The tray 32 is retracted from the reader 20 by the user so as to enable insertion of a test cartridge 20 into the tray for reading and this operation turns the laser light source and related optical components into an ON state and ready for read operations. These operations will be described in detail later in this document.

Figure 5:
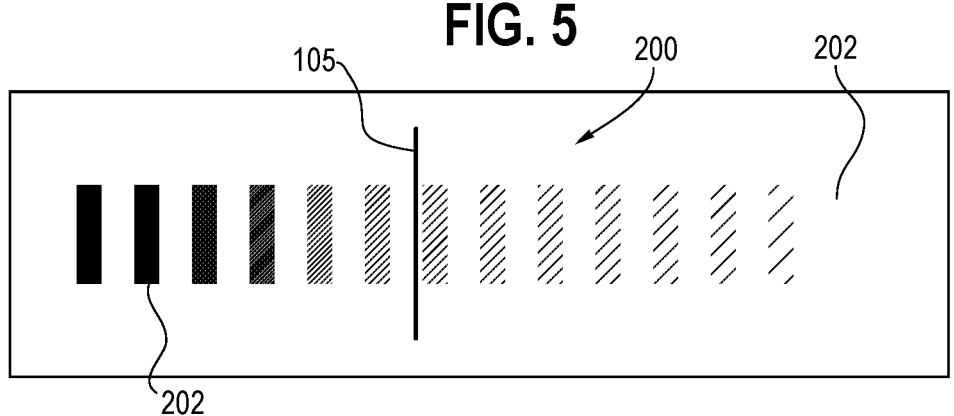
FIG. 5 is an illustration of an optical calibration test pattern that is incorporated into the tray receiving the test device of FIG. 3.
Figure 6:
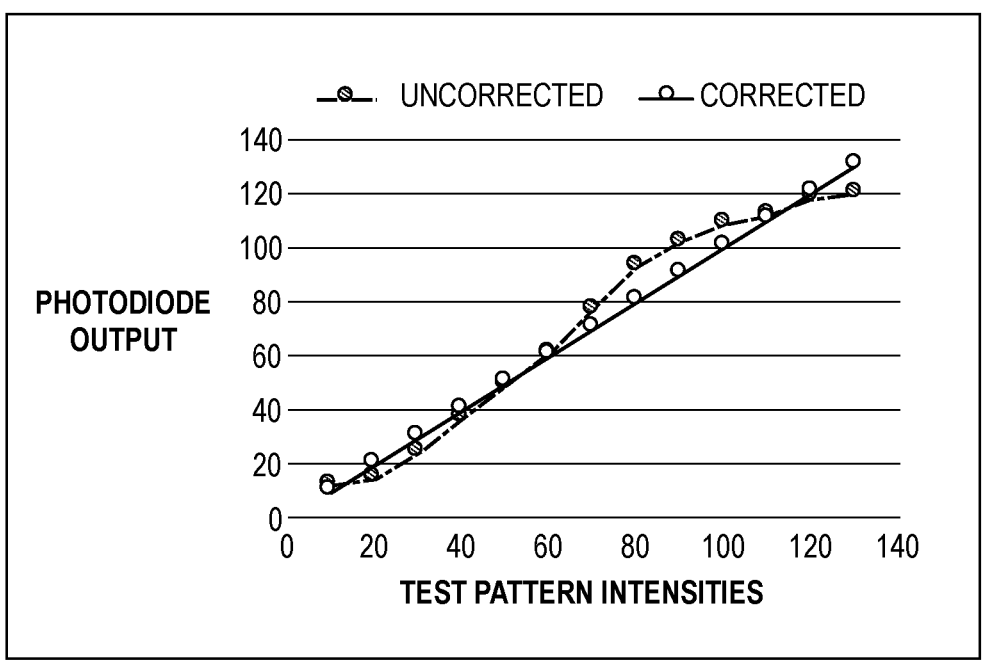
FIG. 6 is a plot of photodiode output as a function of test pattern intensities in accordance with the calibration pattern of FIG. 5, showing how the electronics in the reader can correct the photodiode output signals to match the calibration pattern.
Figure 13:
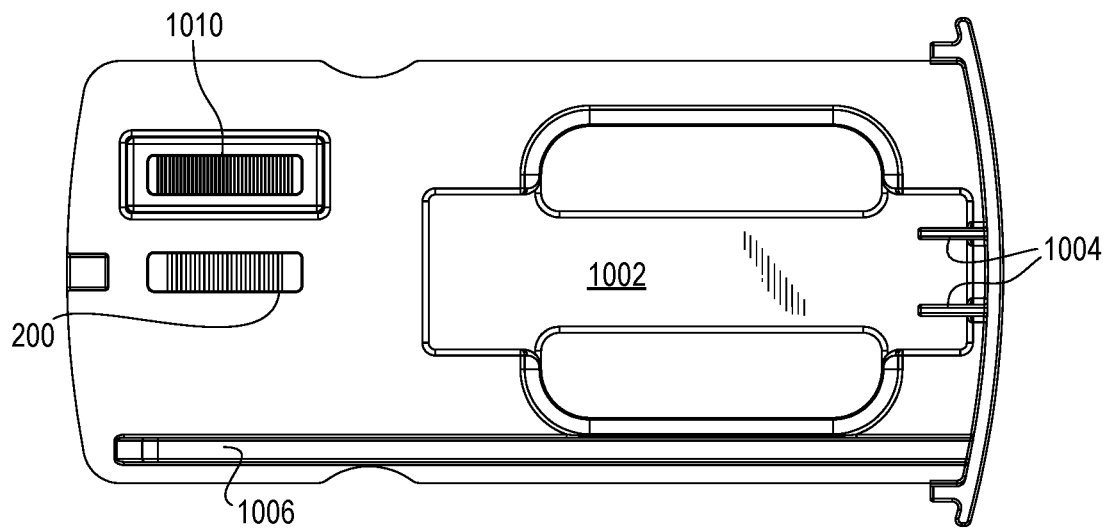
FIG. 13 is a plan view of the tray.
Figure 14:
FIG. 14 is a side view of the tray.

An optical calibration test pattern 200 (see FIG. 5) is affixed on the top surface of the tray 32 in alignment with the long axis of the test strip within the cartridge 20 as shown in FIG. 13. This test pattern can be printed in a controlled manner and affixed as a sticker or insert at a designated location on the tray, see the description below. After the test cartridge 20 is installed in the tray and the tray 32 inserted into the reader, this calibration test pattern enables the reader to perform a sophisticated self-test immediately before the test strip of the cartridge itself is read, described in detail in conjunction with FIG. 8 later in this document. The calibration test pattern (in top view, as viewed by the photodiode) is shown in FIG. 5 and takes the form of a multitude of parallel bands 202 (say 5, or more, or 10 or more, such as 13 or 20) of gradually varying intensity or darkness as shown in FIG. 5. Such bands 202 may be gray-scale or colored, e.g., colored red. The manner of conducting this calibration is described below. Briefly, in one possible configuration, the pattern consists of 13 parallel red lines in a linear series of known, graded intensities from 0.05 to 1.0 with 1.0 being maximum intensity. The lines are oriented in the same direction as the projection of the laser light line 105 onto the test strip. The movement of the tray out of the reader to load the cartridge turns on the reader, which then reads the 13-line test pattern as the pattern moves past the photodiode and just ahead of the inserted cartridge as the cartridge is inserted into the reader. The resulting photodiode output provides a calibration curve that the reader then uses to correct for any non-linear response of the reader's optical or electronic systems, thus insuring that every reader will yield the same readout for a given test cartridge, despite reader-to-reader variations or reader degradation with time. This correction of the test pattern intensity is shown in FIG. 6.

Immediately following the test pattern scan the test cartridge is scanned, yielding a readout like that in FIG. 7A. FIG. 7B shows the same data with a 3-point moving average applied to reduce noise.

During signal processing (see FIG. 9, described below) a peak-finder algorithm identifies the control, and test line peaks, such as IgM, and IgG peaks (left to right in the above example, respectively), if present, based on their expected positions within pre-defined scan position ranges. The areas under these peaks (AUPs) are calculated, including a baseline background subtraction step, and finally the ratios of the IgM and IgG AUPs to that of the control line AUP are calculated. A line is considered 'present' if and only if its peak is identified by the peak-finder algorithm within its expected range of positions, its peak height exceeds an arbitrary pre-set multiple of the baseline noise, and its width at half-height falls within a pre-set range of values.

The results of the test can be reported directly to the user/test administrator by means of a display 34 (FIG. 3) incorporated on the surface of the reader. While a variety of possible reporting mechanisms are contemplated, such as "positive", "negative" or the like, in one possible configuration the results are reported as an alphanumeric indicia, such as "1", "2", "3", "4", or "5", "A", "B" (or some other range of integers or letters), with the number or letter corresponding to a particular interpretation of the test cartridge. The manner of human interpretation of the test result number, e.g. "4", can be done by reference to literature accompanying the reader, by means of a table or explanatory text printed on the reader itself, or in other format. An example of literature for interpretation of the test report number for a COVID-19 test embodiment of the reader is found at the Appendix of our prior provisional. It will be understood that different types of tests will have different interpretation of the scores and the example provided is just one of myriad possible ways in which the test result can be reported to the user. The reporting a number as described above is therefor offered by way of example and not limitation.

With the above description in mind, a more detailed description of the illustrated embodiment will now be set forth. The presently preferred embodiments are offered by way of example and not limitation.

Test Cartridge and Sample Collection

Figure 2A:
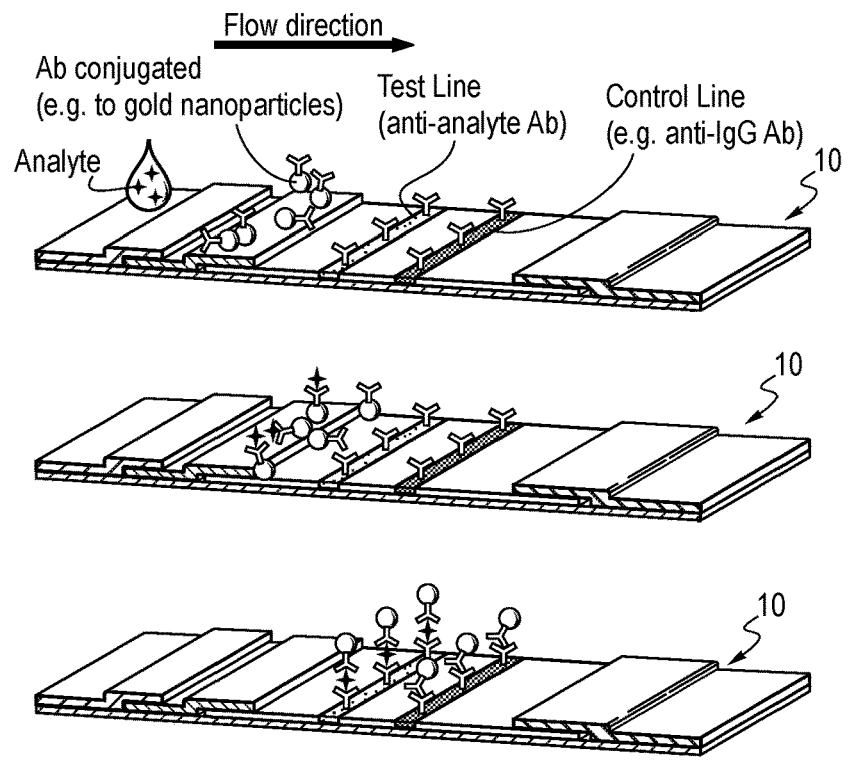
FIG. 2A is a schematic drawing showing the operation of a LFA in three steps. Top: the sample is deposited on the sample pad and migrates towards the conjugate. Middle: the conjugated antibodies bind the target analyte. Bottom: migration to the test line, where the bound target analyte is captured, and the control line. The most commonly used LFA is the pregnancy test (One Step hCG Urine Test), which uses hCG strips. Possible results and interpretation of the test are shown in FIG. 2B. In the case of a weak positive result in a pregnancy test, it is recommended to repeat the test 1 week later.
Figure 2B:
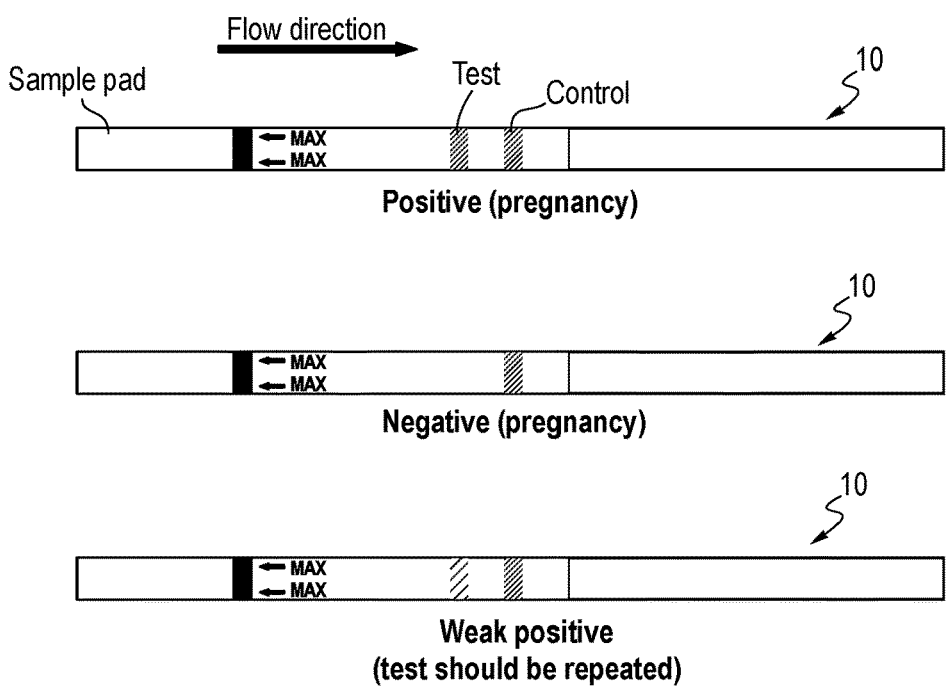
Figure 3A:
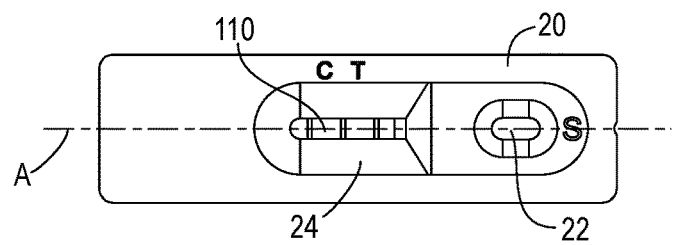
FIG. 3A is a plan view of the test device of FIG. 3.

One form of the test device suitable for use with the reader 30 is shown in FIG. 3 and in plan view of FIG. 3A. The test device is in the form of a cartridge 20 or carrier which holds within it a test strip 110 having one or more test lines and control line shown at 26 and 28 in FIG. 3. The cartridge 20 includes an aperture or opening 24 which reveals the control and test lines enabling such lines to be read by the reader. A sample well port 22 is provided for introduction of a fluid sample (e.g., blood, saliva, etc.) which then is able to migrate through the test strip as explained in conjunction with FIGS. 1 and 2. The test device 20 form factor is not particularly important. The test device includes a long or major axis A coincident with the long axis of the test strip within; the test and control lines are oriented perpendicular to this axis as shown in FIG. 3A.

Reader

Figure 10:
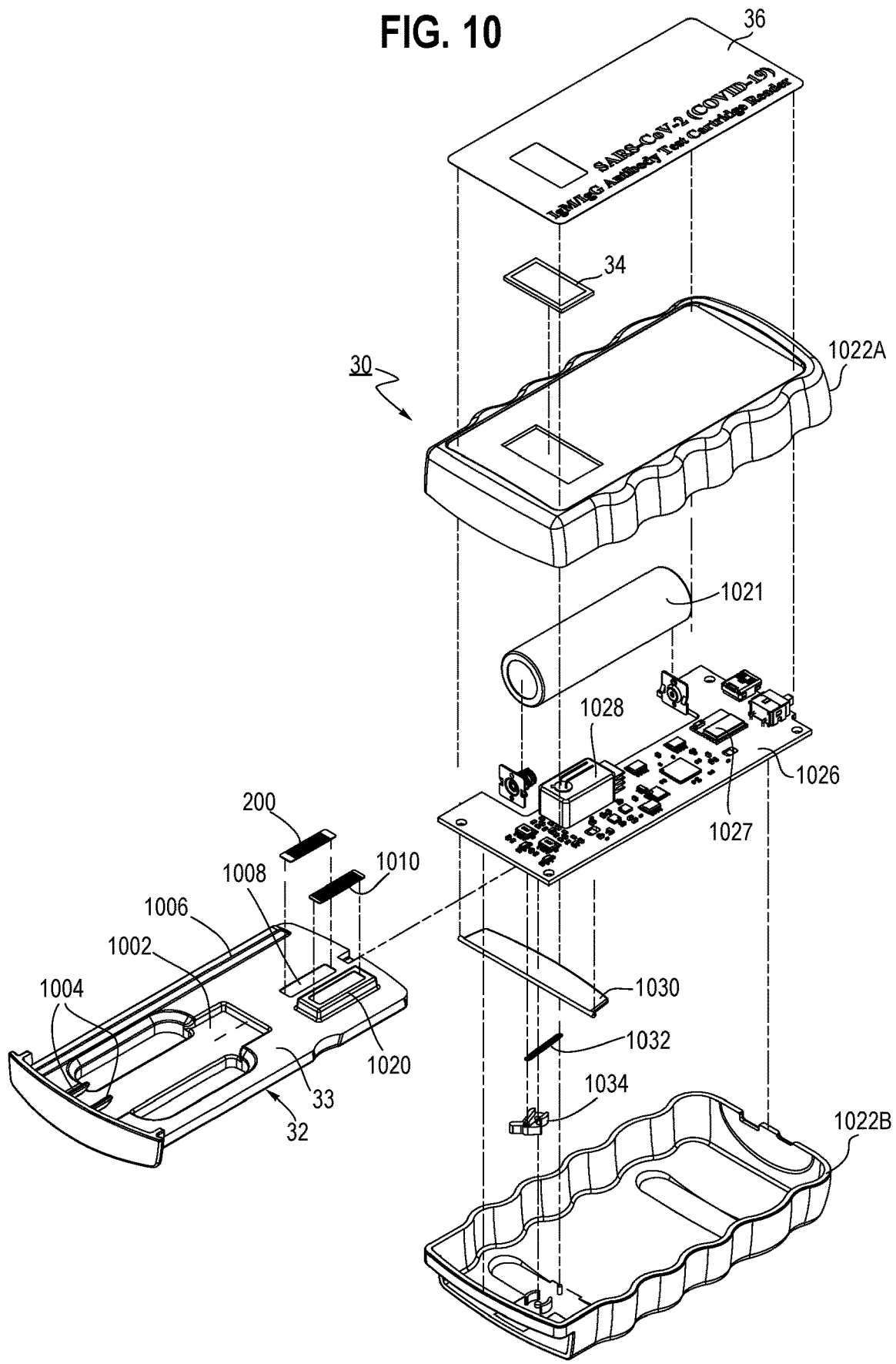
FIG. 10 is an exploded view of the reader of FIG. 3 as seen in perspective view from above.

The reader 30 of FIG. 3 is shown in exploded view in FIG. 10. It includes upper and lower housings 1022A and 1022B, which may be made of molded plastic. The housings enclose a rechargeable lithium ion battery, electronics mounted to a circuit board 1026, including an optics unit 1028 (shown schematically in FIG. 4). The electronics include a programmable microprocessor, memory, A/D converter, and other conventional components, the details of which are not particularly important, or will be described in detail later.

The reader further includes a laser diode light shield door 1030 which deploys (e.g., swings down, using a spring, not shown) when the tray 32 is moved from closed to open positions thereby preventing escape of laser light from the interior of the reader. The light shield door could also be positioned immediately adjacent to the aperture 1102 (FIG. 11) in the board for the light beam, and which slides into and out of positions obstructing the aperture and thus blocking the beam of laser light. Activation of the door could be triggered by a ramp or other feature formed in the tray 32.

Figure 15:
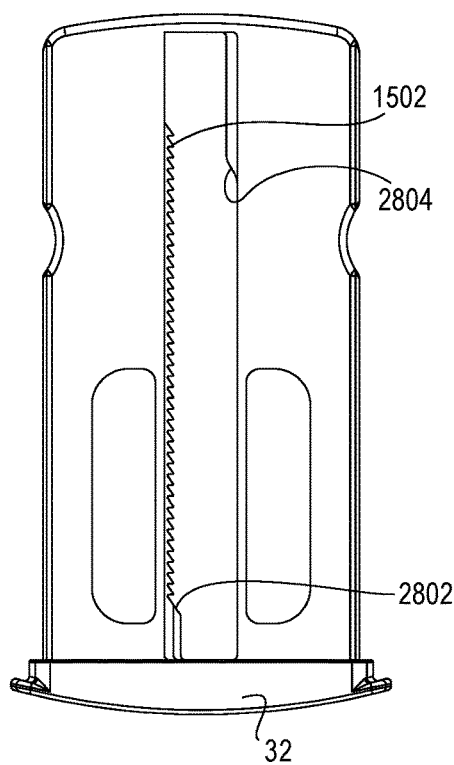
FIG. 15 is a bottom plan view of the tray; in one possible configuration a QR code is placed on the bottom which is read in an accessory device, however the QR code is not shown in FIG. 15.
Figure 16:
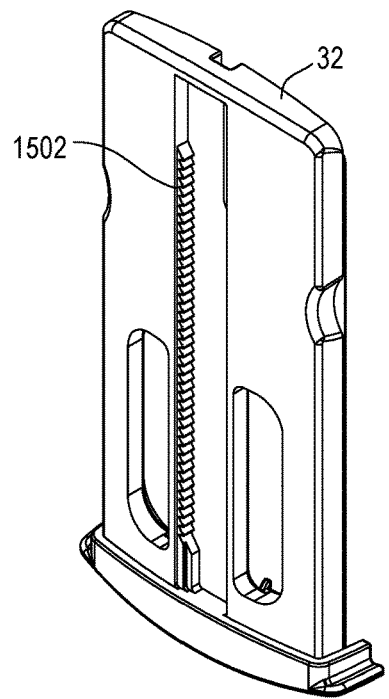
FIG. 16 is a perspective view of the tray from below.
Figure 28:
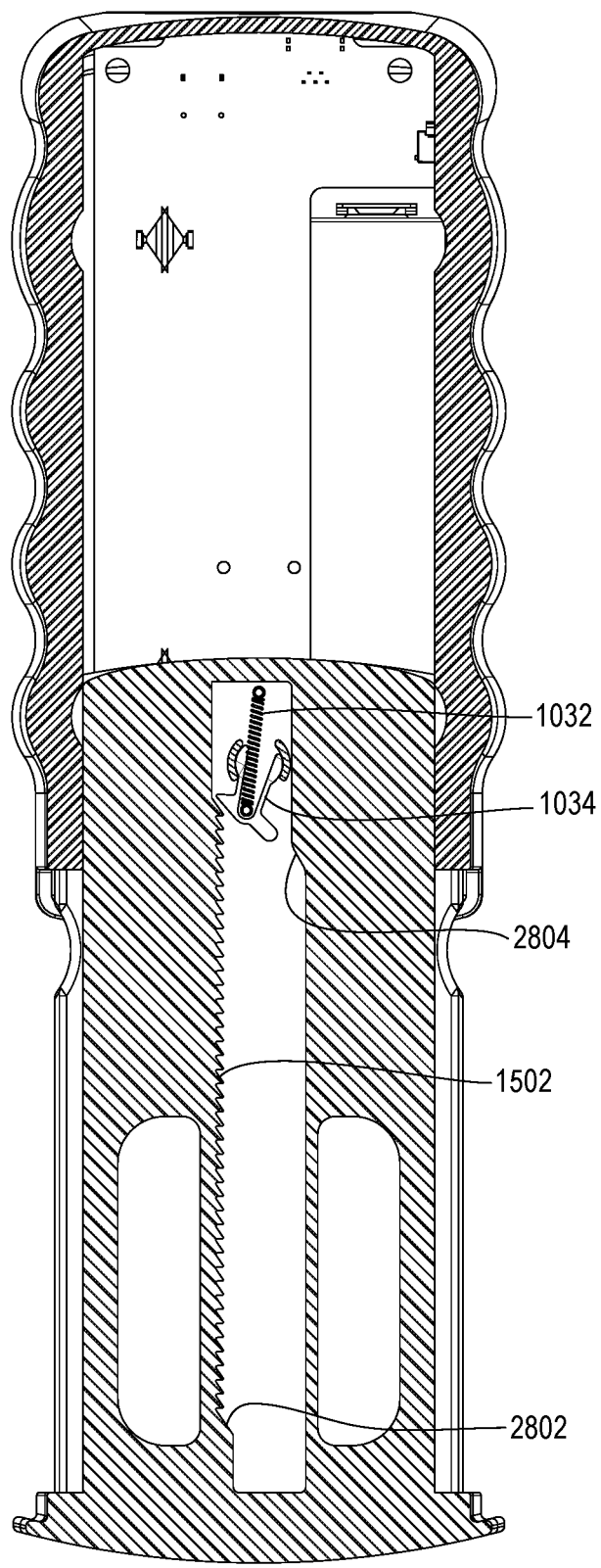
FIG. 28 is cross-section through the reader and tray showing the optional ratchet and pawl mechanism preventing withdrawal of the tray prior to being fully inserted into the reader.

The reader further includes a ratchet pawl extension spring 1032, and a ratchet pawl 1034 which cooperate with a set of ratchet teeth (1502) formed in the tray 32 and shown in FIGS. 15 and 16. When the tray is in the fully withdrawn position the head of the pawl 1034 engages with the first tooth of the ratchet teeth 1502 feature; as the tray is advanced the spring pulls the pawl such that the pawl continues to engage each tooth of the ratchet. When the tray is fully inserted, a ramp 2802 (FIGS. 15, 28) moves the head of the pawl out of engagement with the ratchet teeth thereby allowing the tray to be withdrawn from the reader. When the tray is fully withdrawn a second ramp 2804 moves the head of the pawl back into position to engage the first tooth of the ratchet teeth 1502. Thus, the ratchet feature, pawl and spring cooperate to prevent in-and-out insertion of the tray until the tray is fully inserted, thereby insuring that both the calibration test pattern and all of the test and control lines of the test device are read.

The ratchet, pawl and spring are considered optional and they may not be necessary or provided in the tray and reader in one possible configuration.

Figure 17:
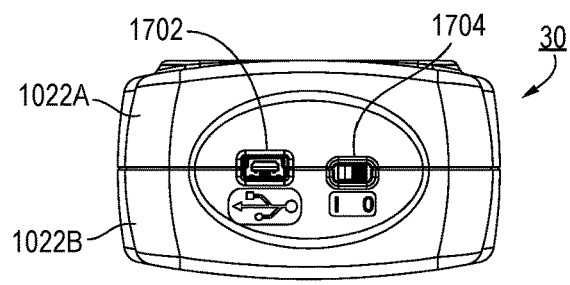
FIG. 17 is an end view of the reader showing a USB port receiving a cable for recharging a battery in the reader, and an on-off switch.
Figure 18:
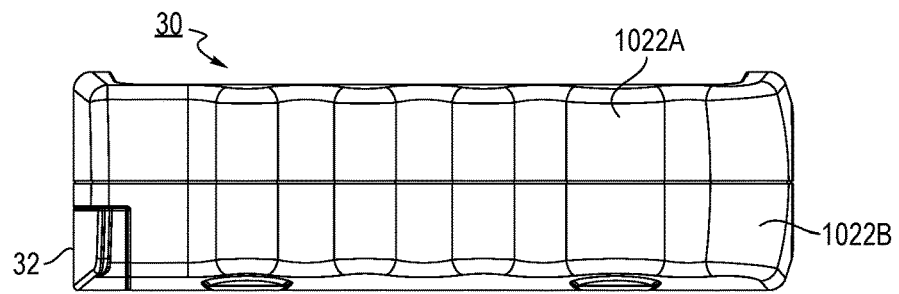
FIG. 18 is a side view of the reader.
Figure 19:
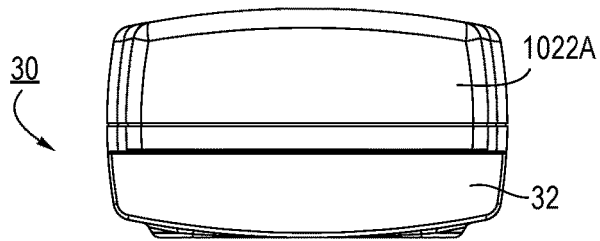
FIG. 19 is an end view of the reader showing the tray closed against the reader.

The rear of the reader (FIG. 17) includes a charging port 1702 for connection to a cable carrying power to recharge the lithium ion battery in the reader. This charging port could for example take the form of a USB port. An on-off switch 1704 is also provided to turn the reader on and off.

The reader housing includes a series of raised and indented portions or grips 2002 (FIG. 20) on the sides thereof to facilitate holding of the reader with one hand.

A. Tray and Test Cartridge Positioning

Figure 22:
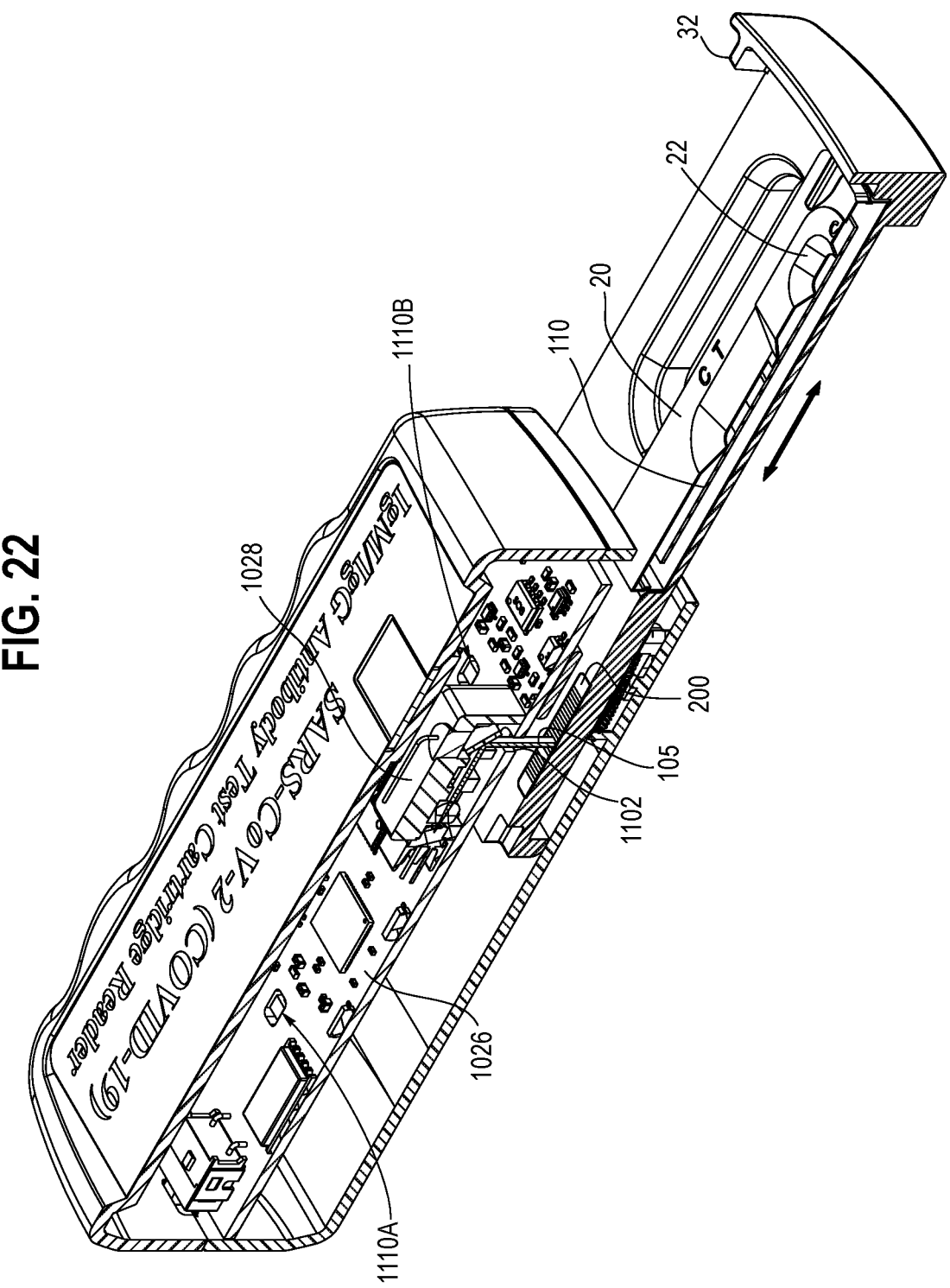
FIG. 22 is a cross-section through the reader with the tray carrying a test strip and the tray partially inserted into the reader to a position where the calibration pattern is read by the optics of FIG. 4.

Referring to FIGS. 3 and 10-22, the tray 32 is extendable from the reader housing between closed and open positions; in the open position the tray receives the test device 20 as shown in FIGS. 3 and 22. The tray 32 includes a ramp 1006 (FIG. 10) which activates limit switches 2400 and 2402 mounted to the electronics board 1026 to turn on and off the optics. In particular, as the tray is inserted into the reader, when the leading edge of the ramp 1006 advances within the reader and contacts the rear limit switch 2400 (FIGS. 11, 22), the laser diode power is activated. During withdrawal of the tray, when the leading edge of the ramp 1006 contacts the front limit switch 2402 (FIGS. 11, 22), the laser power is disabled.

Figure 12:
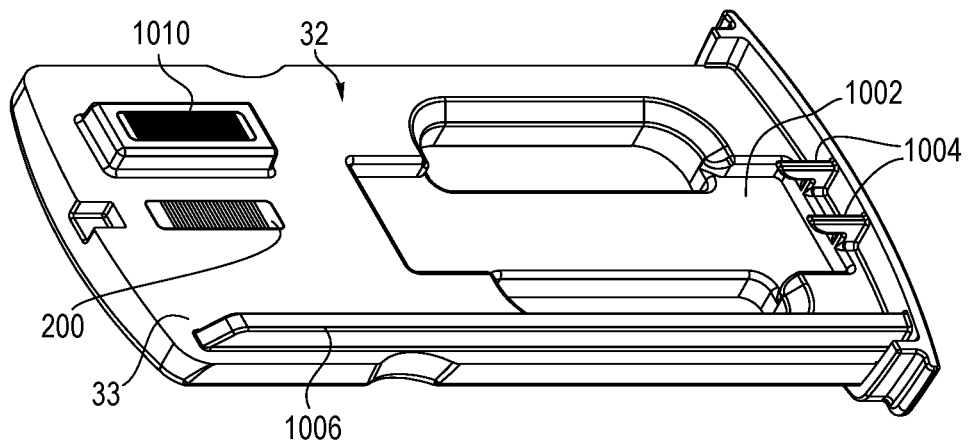
FIG. 12 is a perspective view of the tray of FIG. 3 shown isolated from the reader and showing the test calibration pattern of FIG. 5 and a position encoder pattern on the top surface of the tray.

Referring to FIG. 10, the tray includes a depression or cavity 1002 which has dimensions and form factor to receive snugly the test device 20. The test device is inserted such that the upper surface thereof is retained snugly by two cleats 1004. The upper surface 33 of the tray 32 includes an area 1008 which receives the calibration test pattern 200 of FIG. 5. The test pattern can take the form of a printed sticker or card with adhesive backing printed with the graduated bands as shown in FIG. 5. This area 1008, which may a slight depression molded in the top surface 33 of the tray, facilitates placement of the calibration test pattern 200 in alignment with the axis A of the test strip and the cartridge 20 (FIGS. 3A, 12). The tray further includes a raised mount or platform 1020 to which is affixed an optical position encoder or pattern 1010 which is used for correlating test readings with linear positions during read operations, as explained below.

Figure 11:
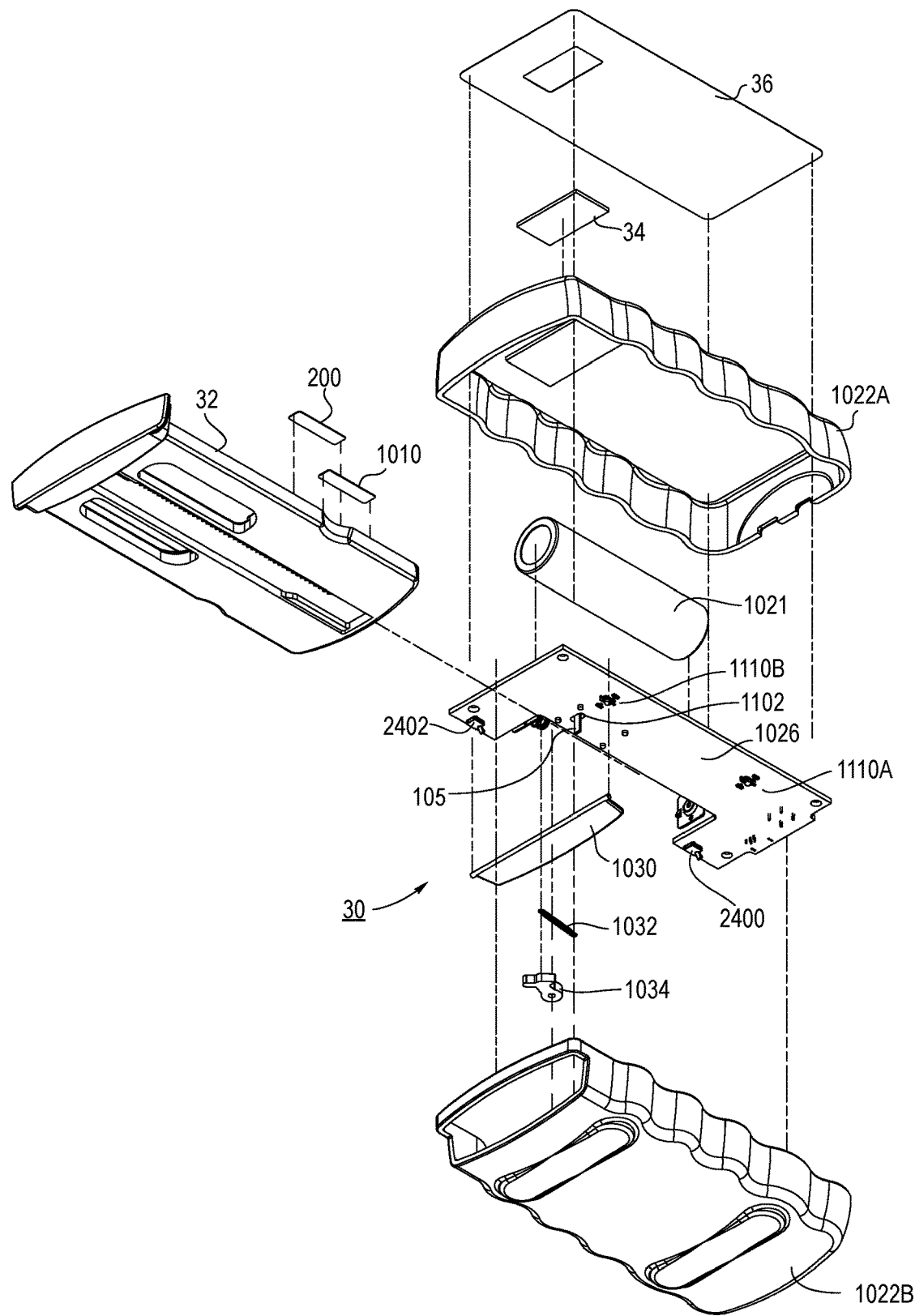
FIG. 11 is an exploded view of the reader of FIG. 3 as seen in perspective view from below.

As shown in FIG. 11, the board 1026 includes an aperture 1102 therein which allows the narrow line of laser light to pass through the board and onto the calibration test pattern and test strip and thus enabling reading of both.

B. Tray Position Detection in Reader

Figure 29:
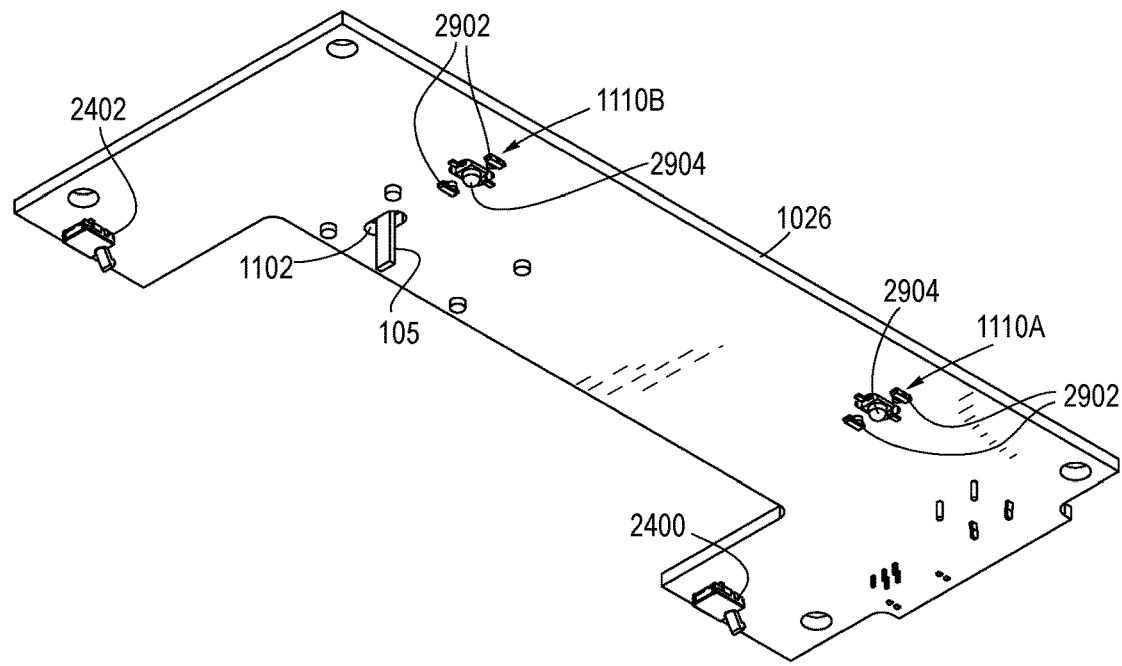
FIG. 29 is a perspective view of the electronics board of the reader showing more detail the photodiode and LED assemblies which are used for reading the position encoding strip on the tray during insertion of the tray into the reader.

Detection of the position of the tray 32 (and associated test cartridge 20) is facilitated by the optical encoder 1010 of FIG. 10 and associated reader assemblies for the optical encoder. These reader assemblies 1110A and 1110B are shown in FIGS. 11 and 29; each of which includes a photodiode 2904 and two LEDs 2902. These photodiodes are positioned off-center and in alignment with the encoder 1010 placed on the top surface of the tray such that as the tray is inserted into the reader the encoder is illuminated by the LEDs 2902 and the reflectance from the encoder 1010 is read by the associated photodiode 2904. The platform on which the encoder 1010 is affixed serves to raise up the encoder to an elevation immediately below the photodiode such that the field of view of the photodiode encompasses a single stripe or band of the encoder 1010.

C. Optics Unit

Figure 26:
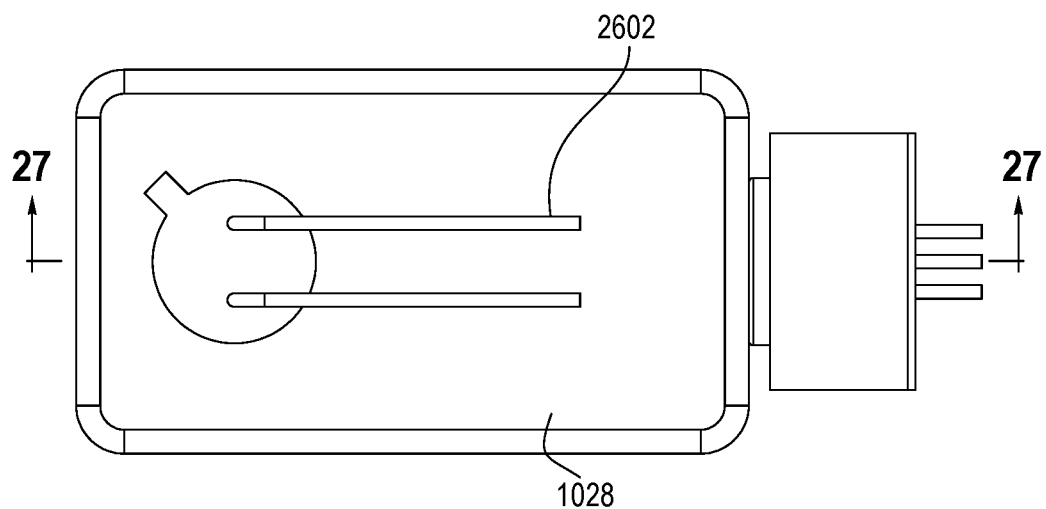
FIG. 26 is a plan view of the optics unit in the reader.
Figure 27:
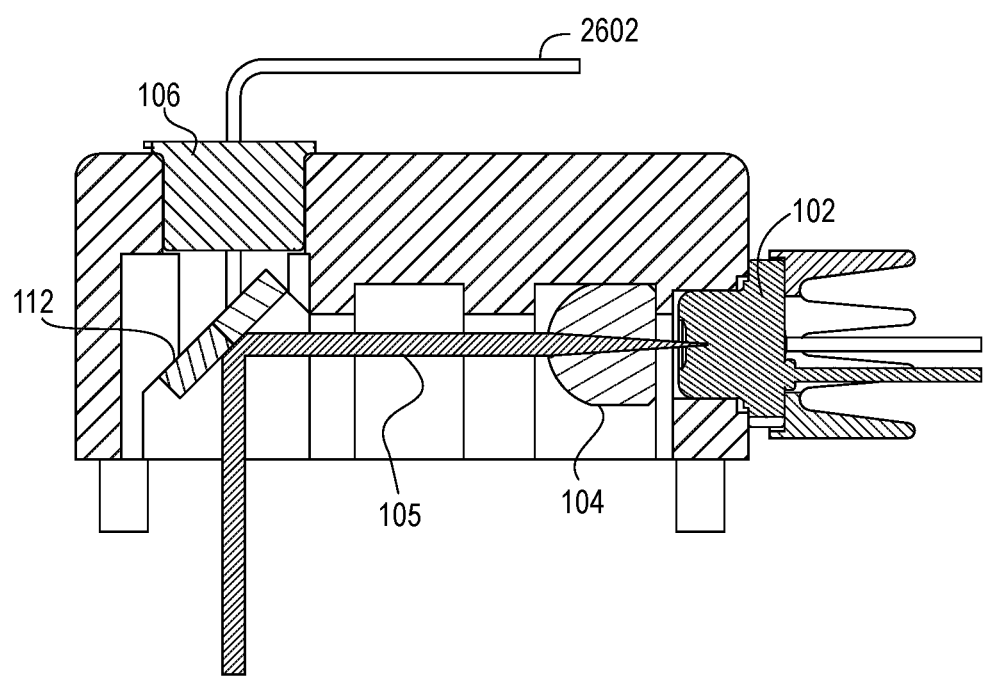
FIG. 27 is a cross-section through the optics unit of FIG. 26 taken along the lines 27-27 of FIG. 26.

The optics unit 1028 (FIGS. 10, 22) is shown schematically and operation thereof is discussed previously in conjunction with FIG. 4. The unit 1028 is shown isolated in plan view in FIG. 26 and cross-section in FIG. 27. The unit 1028 includes the laser diode light source 102, a lens 104 converting the Gaussian dot output of the laser diode into a line format 105 (e.g., 2 mm by 50 µm), with optional use of baffles or other beam shaping elements in the unit 1028. As shown in FIGS. 4 and 27, light reflected from the test strip and calibration pattern passes through the half-slivered mirror 112 and impinges on a (single) photodetector 106. Heat sinks 2602 dissipate excess heat from the photodetector 106.

The laser diode light source 102 has an output wavelength that is optimized for the chemistry of the test strip and test under consideration, e.g., the size and characteristics of the particles (e.g., gold nanoparticles) that bind to antigens or other analytes in the test sample. An output wavelength in the range of 520-540 nm is one presently preferred embodiment of the reader and test device, in which the IgG and IgM antibodies of the SARS-Cov-2 virus bind to colloidal gold-labeled SARS-CoV-2 antigen on the test lines of the test strip.

D. Calibration

Figure 8:
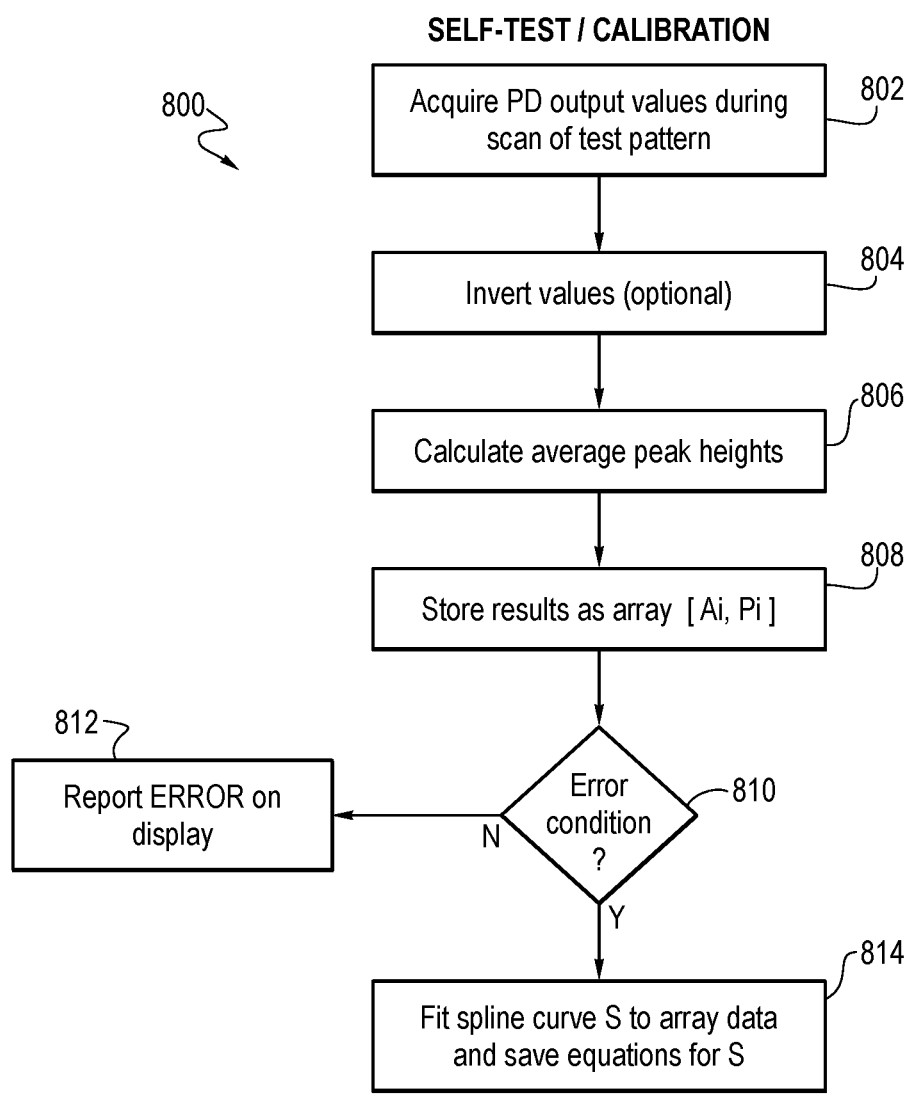
FIG. 8 is a flowchart showing a sequence of processing operations performed within the reader in a self-test or calibration procedure.

FIG. 8 is a flowchart showing a sequence of processing operations 800 performed within the reader in a self-test or calibration procedure. The procedure of FIG. 8 is performed as the tray 32 containing the test cartridge 20 is manually inserted into the reader 30 and as the calibration test pattern 200 of FIG. 5 placed on the top of the tray moves past the photodiode detector position within the reader. See FIG. 22.

At step 802, a 1×N array of photodiode output values is acquired as a function of scan position along the test pattern.

At step 804, an optional step is performed of inverting the array's values by dividing 1 by each data value (1/datum). This step is for conceptual simplification only; it converts negative-going valleys in the photodiode output (corresponding to red test pattern bands or stripes) to positive-going peaks.

At step 806, the processing identifies the 13 rectangular pulses in the data (corresponding to the 13 bands in the calibration pattern) and calculates their average heights, by applying an amplitude discrimination (rather than differentiation) peak-finder algorithm. An implementation of such a pulse-finder, in Matlab format, is available online at https://terpconnect.umd.edu/-toh/spectrum/findsquarepulse.m, but of course other procedures could be used.

At step 808, the processing stores the result of Step 804 as a 14-member array, $[A_i, P_i]$, where i=1 ... 14, and where $A_i$=-(% absorbance) of the ith test pattern line, as printed (14th member=test pattern background), and $P_i$=average peak height of the ith test pattern line's photometric read.

At step 810, a check is made to see if an error condition is present. Failure to identify all 13 peaks is considered a reader error condition, as is also the case if any or all peak heights are outside of an allowable range (empirically pre-determined, and the associated parameter stored in memory of the reader). If an error condition is present the processing proceeds to block 812 and an error condition is reported on the reader display.

If no error condition is present, the processing proceeds to block 814. In this step, a cubic spline curve S with 14 "knots" and 'natural spline' boundary conditions, see FIG. 6, is fitted to the data of the array of step 808. An example of the calculation of the cubic spline curve is at https://timodenk.com/blog/cubic-spline-interpolation/. The system of equations defining the spline curve will be used to interpolate normalized absorbance values for the photometric data from the cartridge scan in the Cartridge Data Processing of FIG. 9, below. Thus, the equations for the cubic spline curve S are saved in memory of the reader. In essence the spline curve S acts to correct the photodiode readings for any nonlinearity in the reader optics or electronics.

E. Reading Operation and Related Calculations

Figure 9:
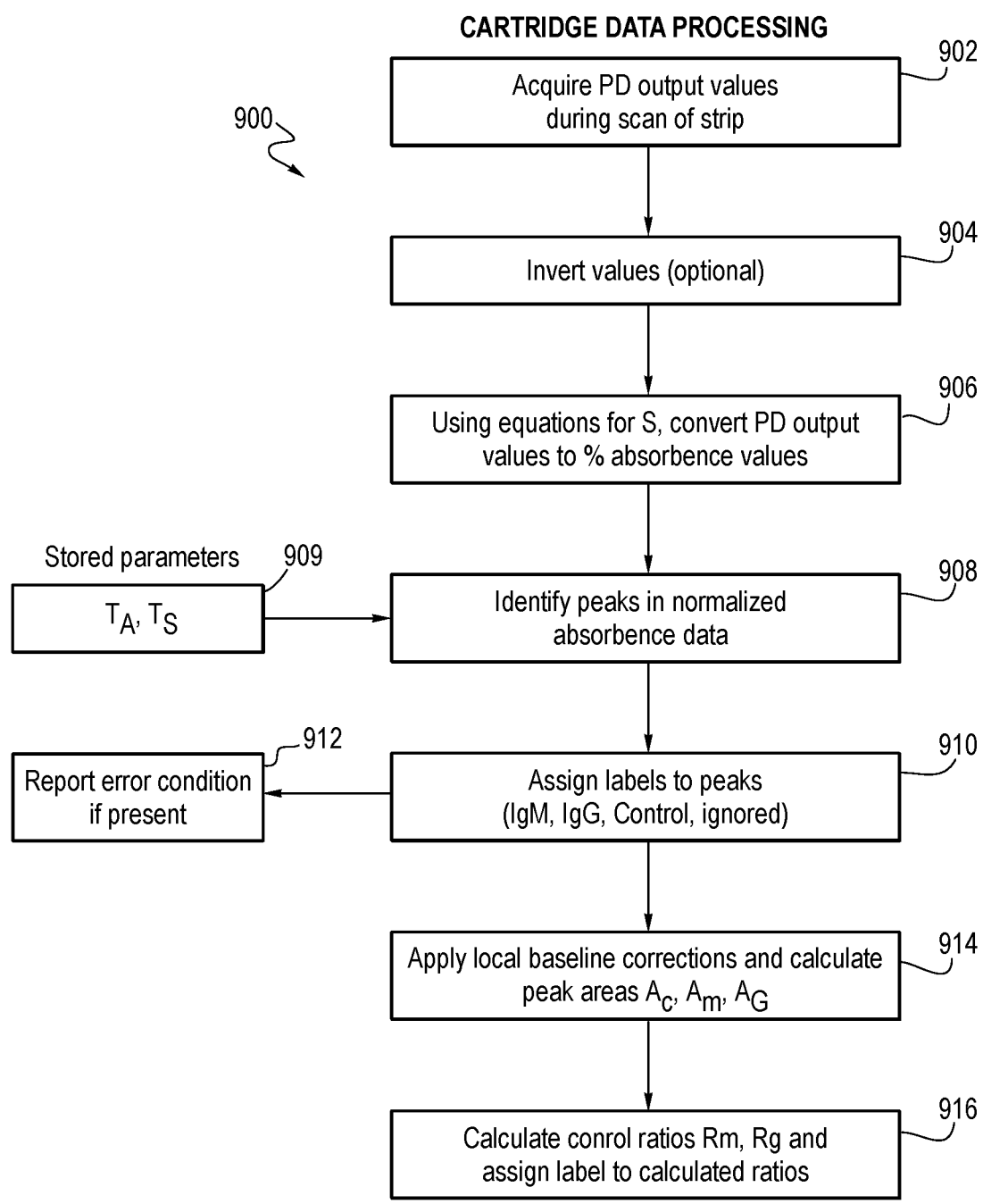
FIG. 9 is a flowchart showing a sequence of processing operations performed within the reader during the operation of reading the test strip within the cartridge.
Figure 23:
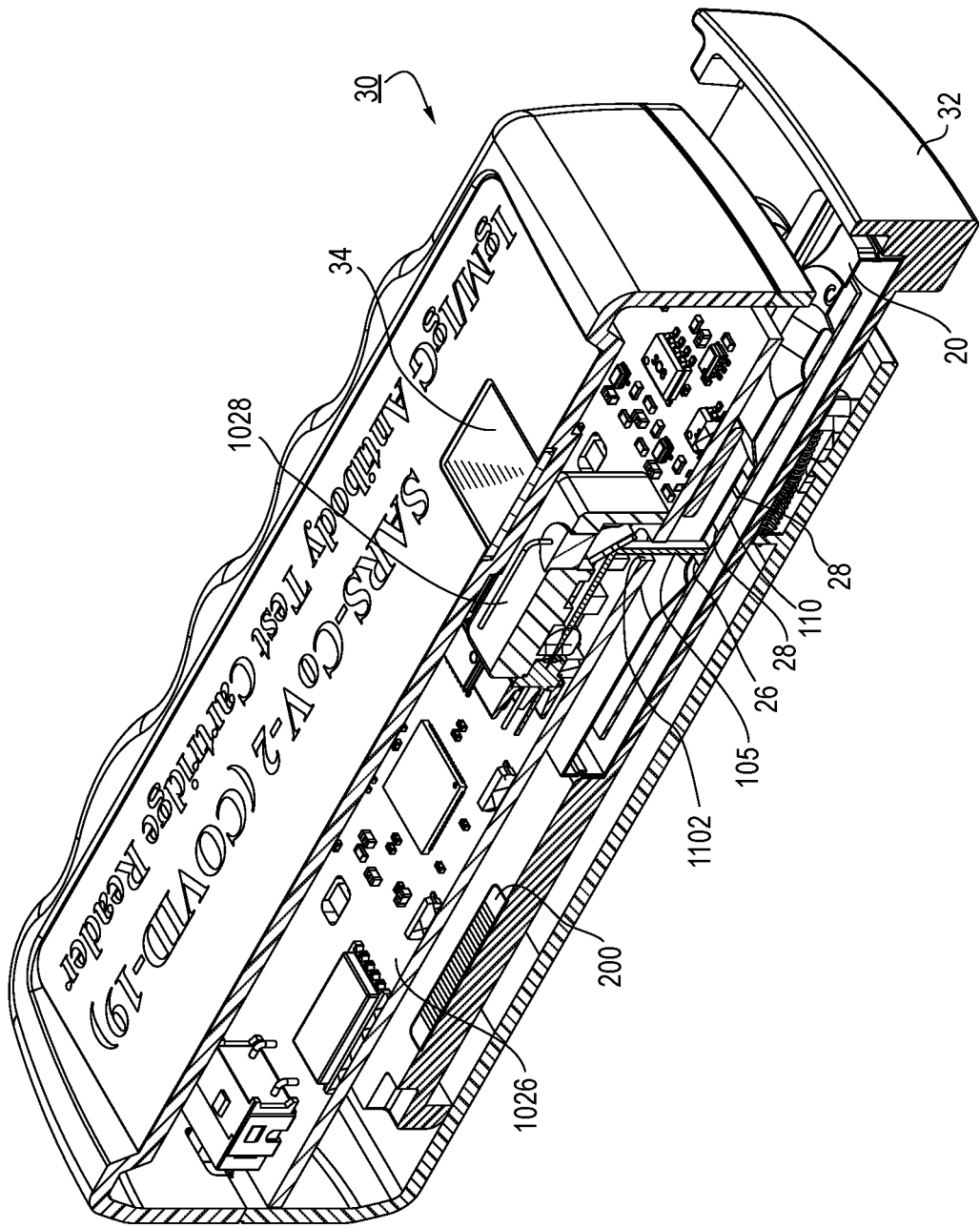
FIG. 23 is a cross-section through the reader with the tray carrying a test strip and the tray more fully inserted into the reader as compared to FIG. 22 to a position where the control line of the test device 20 is being read by the optics in the reader.
Figure 24:
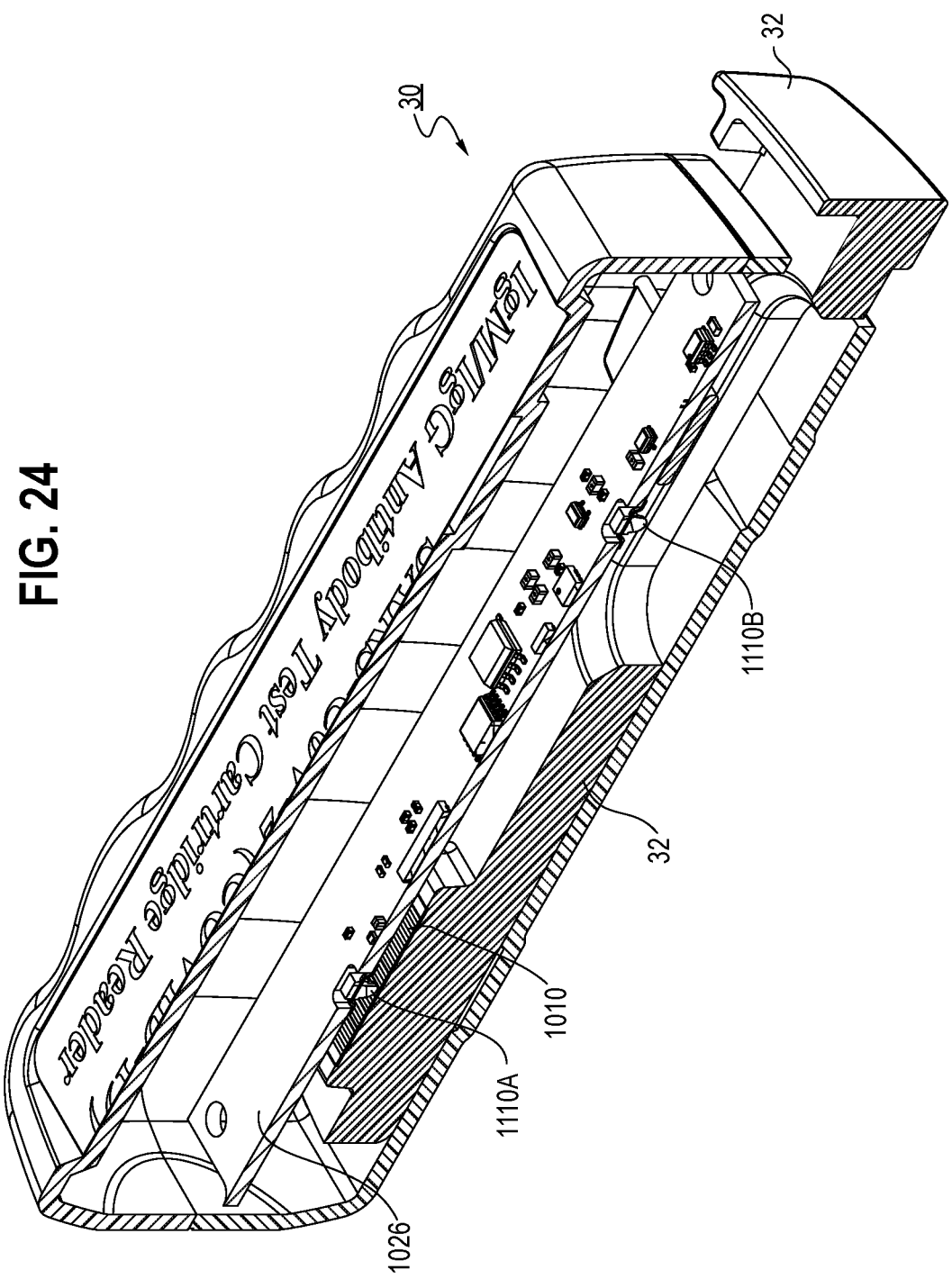
FIG. 24 is a cross-section through the reader with the tray inserted into the reader in roughly the same position as compared to FIG. 23, showing the reading of the position encoding pattern affixed to the tray, as shown in FIG. 12. The test device is omitted in this view.

As the cartridge is inserted into the reader past the point where the calibration pattern (FIG. 5) read by the photodiode (and the above calibration is performed), the area of the test strip with the control and test lines is then in position for reading. See FIG. 23. At this point, the cartridge data processing operations 900 of FIG. 9 are performed.

In particular, step 902 is Cartridge Data Acquisition: Acquire a 1×N array of photodiode output values as a function of scan position along the cartridge's nitrocellulose strip 110 (FIG. 3, 4).

At step 904, an optional step is to invert these values by dividing 1 by each data value (1/datum). This step is for conceptual simplification only; it converts negative-going valleys in the photodiode output (corresponding to positive test lines and the control line) to positive-going peaks.

At step 906, using the system of equations describing the spline curve S fitted to the test-pattern data above and stored in step 814 of FIG. 8 (Self-Test/Calibration Processing), these photodiode output values are converted to % absorbance values.

At step 908, peaks in the normalized absorbance data of 906 are identified by applying a first derivative zero-crossing peak finder. Briefly, this involves calculating the first derivative of each point in the ordered series (optionally employing smoothing coefficients, if required for noise reduction) and identifying as peak maxima those points whose derivatives:

1. have downward-going zero crossings;
2. and have slopes exceeding a predetermined slope threshold, $T_S$.
3. at a point where the original signal's amplitude exceeds a predetermined amplitude threshold, $T_A$.

The values of $T_A$, $T_S$, and the smoothing coefficients are determined empirically, based on observation of numerous test cartridges, to yield peak identifications conforming with trained observers' judgments and/or orthogonal test results such as enzyme-linked immunoassays (ELISA) of the same blood. As such, these parameters are determined in advance and stored in memory of the reader as indicated at 909. These empirical observations benefit from our ability to test negative blood samples spiked with known amounts of antibody, thus ensuring that our predetermined thresholds and coefficient values do not exclude identification of weak true positive peaks (to minimize false negatives) or include identification of weak stains as peaks (to minimize false positives).

At step 910, labels are assigned to the peaks defined in the above steps. The labels assigned are either as Control, IgM, or IgG peaks, or ignored, provided they fall within pre-defined windows of scan positions (based on empirical observations of line locations in numerous test cartridges from several batch numbers). It should never be the case that two peaks are identified within one window. If this occurs, it is considered a cartridge error condition. If such an error condition is detected it is reported as indicated at 912.

At step 914, the processing applies local baseline corrections to the Control, IgM and IgG peaks defined above (e.g., background subtraction) and calculates peak areas (same as area under the peak, AUP) $A_C$, $A_M$, and $A_G$, respectively, treating the peaks as Gaussian in shape. Code examples are known in the art to persons of ordinary skill; for one in Matlab see, e.g. https://terpconnect.umd.edu/-toh/spectrum/findpeaksb.m.

At step 916, the processing calculates test line peak to control line peak ratios $R_M$ and $R_G$ as $R_M = A_M/A_C$ and $R_G = A_G/Ac$. These ratios are then used to report test results to the user, e.g., via the display 34 or by the use of a reporting of a number on the display 34 which has to be cross-referenced to instructions or literature for interpretation. For example, in the COVID-19 scenario, ratios above an empirically determined preset threshold (again, determined in advance and stored in memory) are considered 'antibody-positive' results for IgM or IgG, respectively. Alternatively, ratios falling within pre-defined ranges may be classified as (e.g.) 'high positive,' 'medium positive', or 'low positive'.

F. Positioning

As noted above, in both the calibration step and in the reading operation the reader acquires a 1×N array of photodiode output values as a function of scan position. The photodiode output values for position are obtained from the photodiodes 2904 in the assemblies 1110A and 1110B, see FIG. 29.

Figure 25:
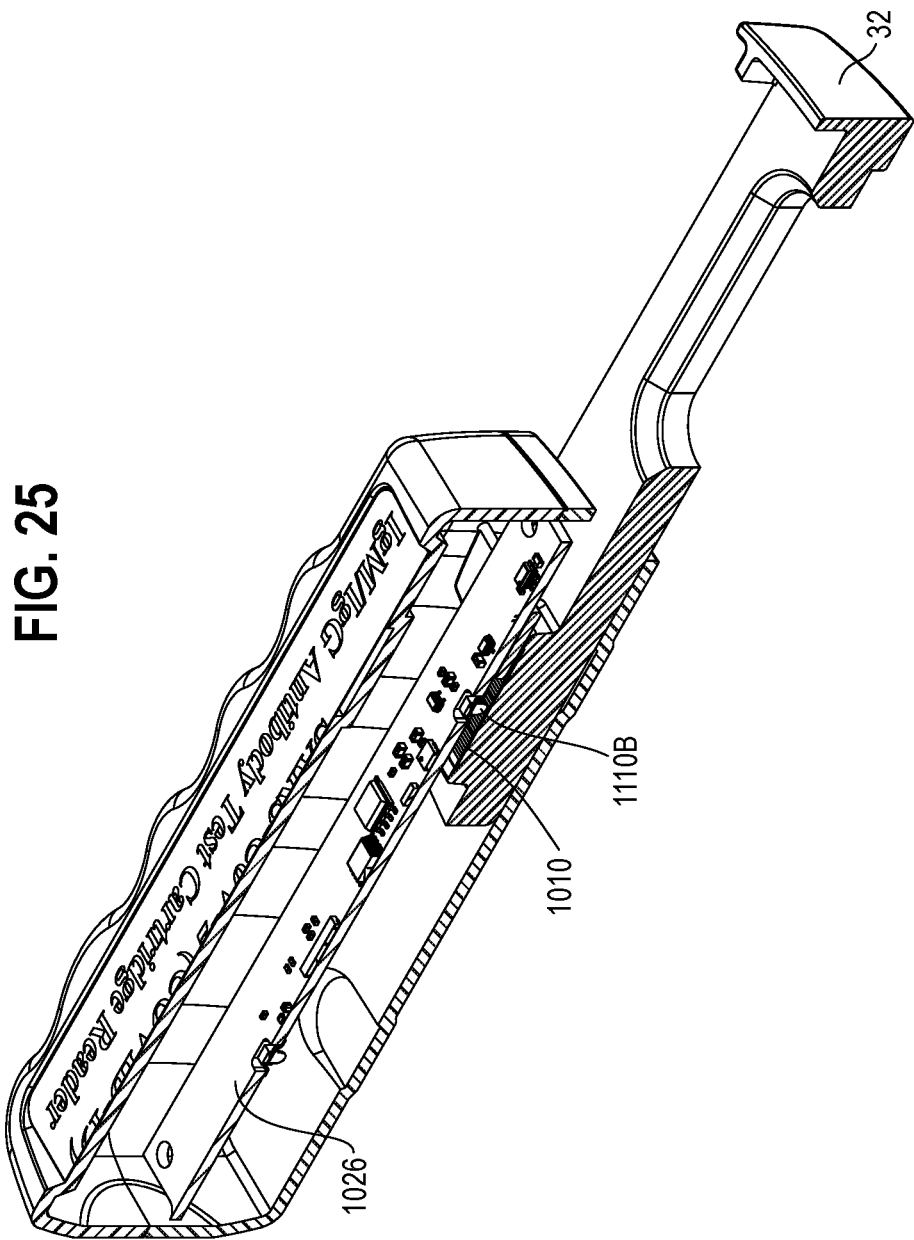
FIG. 25 is cross-section through the reader showing the tray partially withdrawn from the reader. The test device is omitted in this view.

This positional relationship between photodiode output and scan position is accomplished by providing on the cartridge tray 32 a series of ruled registration marks—thin black lines spaced at (e.g.) 1 mm (or, preferably 0.5 mm) intervals, hereinafter the "encoder strip" 1010, see FIGS. 12, 13 and 25. In one possible arrangement, the encoder strip 1010 can be produced as an adhesive sticker which is permanently affixed to the top face of the carrier during manufacturing of the tray. To keep manufacturing costs low, the positioning of the encoder strip on the tray need not be highly precise, e.g., requiring a jig or an alignment tool during the carrier manufacturing process. Thus, the signal processing algorithm outlined below does not require precise knowledge of the start- and end-points of the encoder strip with respect to the expected positions of the test and control lines on the cartridge's nitrocellulose strip. Instead, it is sufficient that the sample encoder strip merely spans the same length as the region of interest (ROI) of the nitrocellulose strip (the length spanned by the Control, IgM and IgG test stripes) without spanning the ends of the nitrocellulose viewing window of the cartridge, and be reasonably parallel to the nitrocellulose strip 110 (FIG. 3). Optionally, a second encoder strip spans the length of the test pattern (without spanning the ends of the test pattern sticker) and is reasonably parallel to it, as well. In one embodiment these encoder strips are illuminated by LED(s) and read by a single photodiode each, masked or otherwise having a field of view encompassing only a single registration mark at a time as the carrier is inserted into the reader. This is the preferred arrangement shown in FIG. 11 at 1110A and 1110B.

Registering photodiode output with respect to position along either the nitrocellulose strip, or the test pattern, thus involves simultaneously reading the outputs from the sample photodiode (FIG. 4, 106) and the encoder photodiode 2904 of assemblies 1110A or 1110B (FIG. 11, 29). Thus, in the illustrated embodiment, the spacing of the encoder pattern 1010 and its associated photodiodes in the assemblies 1110A and 1110B is such that the calibration test pattern and test strip are read by the sample photodiode 106 at the same time as the encoder pattern is read by the encoder photodiode in the assembly 1110A or 1110B.

The following procedure is then conducted:

1. A 2×N array of sample photodiode (106) output values and time-matched encoder photodiode (1110A, 1110B) output values (hereinafter "the data array") is stored in memory. Each element in this array comprises an equal time interval, i.e., equal to the temporal resolution of the sample photodiode's A/D converter.
2. The amplitude discrimination peak finder algorithm of step 806, described above, is used to identify each registration line in the encoder photodiode's output.
3. The total number of registration lines thus identified is counted. If this number differs from the known total number of registration lines printed on the encoder strip this constitutes an error condition—either the carrier was not inserted all the way into the reader (typically yielding too few encoder lines identified) or else the carrier was partially withdrawn from the reader at one or more points during full insertion (typically yielding too many encoder lines identified, as the encoder strip moves forwards, then backwards, then forwards again across the photodiode's field of view during insertion).

4. The encoder data is linearized with respect to time, in order to correct for possible variation in the speed at which the carrier was inserted into the reader. This step comprises the following sub-steps:

a) Calculate the median and maximum peak widths of the detected encoder peaks.

b) A maximum peak width greater than a specified threshold value constitutes a user error (the user interrupted the insertion process for an unacceptably long interval).

c) Adjust all encoder line peak widths to equal the median peak width, by applying the mathematical operations of erosion or dilation (erode the too-wide peaks and dilate the too-narrow peaks to each equal the median peak width). For an outline of erosion and dilation algorithms see https://www.r-project.org/nosvn/pandoc/mmand.html. Our implementation will use a pre-defined kernel value [for example, (1,1,1)] empirically determined to give the optimal result.

d) Apply the same erosion or dilation functions to the time-corresponding sample photodiode outputs.

e) Calculate the median and maximum inter-peak widths of the detected encoder peaks.

f) A maximum inter-peak width greater than a specified threshold value constitutes a user error (the user interrupted the insertion process for an unacceptably long interval).

g) Adjust all encoder inter-peak widths to equal the median inter-peak width by deleting values from too-wide inter-peak regions or inserting additional values into too-narrow inter-peak regions (the inserted values equal the mean of the two values immediately adjacent to the inserted cell).

h) Apply the same insertion or deletion operations to the time-corresponding sample photodiode outputs.

G. Display

Figure 20:
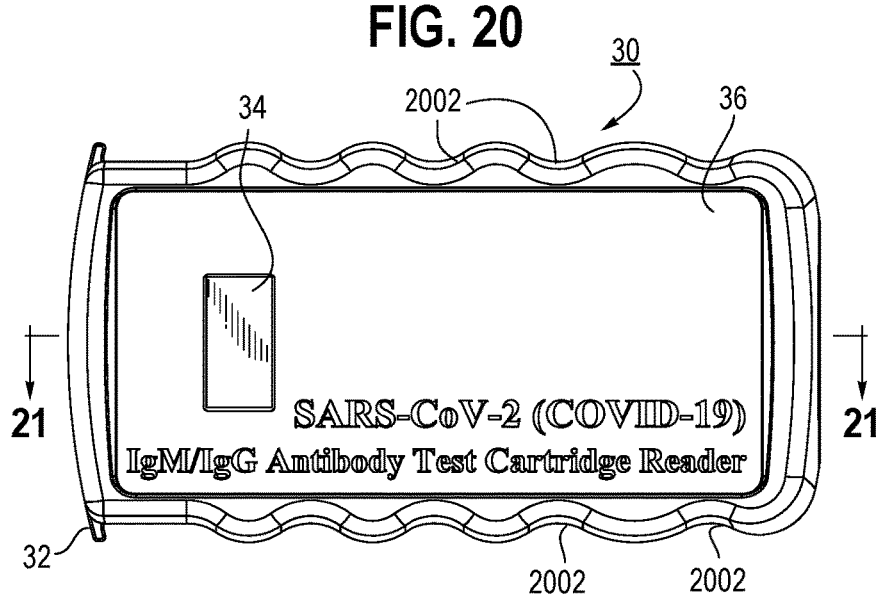
FIG. 20 is a plan view of the reader.
Figure 21:
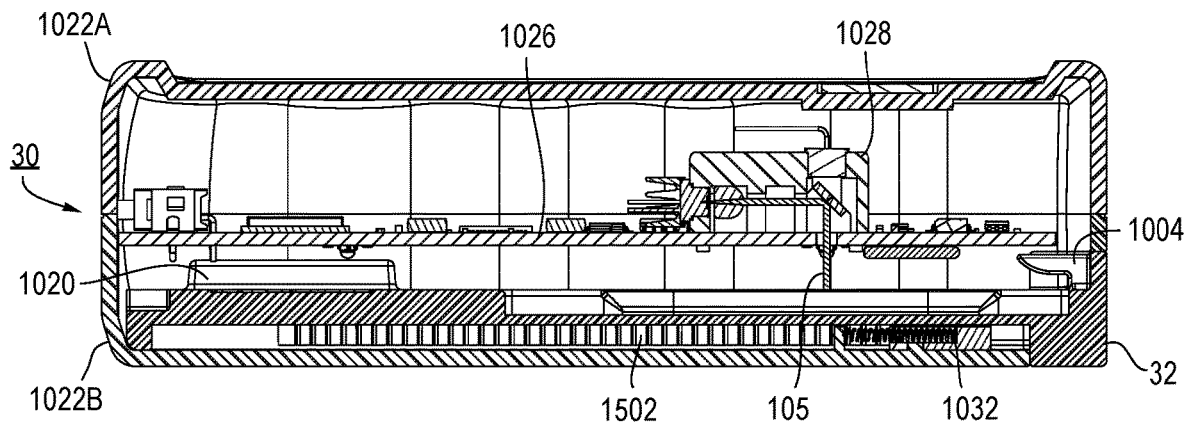
FIG. 21 is a cross-section through the reader along the lines 21-21 of FIG. 20.

As shown in FIGS. 3 and 20, the reader includes a display 34 (which may take any convenient form such as LCD or other), on which the results of the reading operation are displayed to a user. The display 34 could be programmed to display "positive" "negative" "error" or similar nomenclature, or could be programmed to display an alphanumeric indicia, such as "1", "2", "A", "B" etc. which requires reference to external information in order for a user to interpret the results. For example, such external information could take the form of a chart or the like printed on the top of the reader or in accompanying literature, such as shown in the Appendix of our prior provisional application.

H. Reader Electronics and Power Supply

The reader 20 includes electronics mounted to the board 1026 as shown in FIG. 10; such electronics could include a programmable processor or processing unit to perform calculations and generate results as explained in this document and the Appendix of our prior provisional application. Additionally, the electronics will include a memory storing parameters used in the calculations, as explained above, program code, etc. The electronics further include a rechargeable battery 1021 (FIG. 10), a power supply to recharge the battery via the port 1702 of FIG. 17, analog to digital converter(s), and additional conventional components the details of which are conventional and not particularly important. Optionally, the reader includes a GPS unit; files of test results include the GPS location of the reader, as shown in FIG. 41.

I. Interface to Remote Computing Devices

The electronics further includes a wireless transmitter 1027 (e.g., Bluetooth, WI FI or the like) which serves to transmit test results from the reader to an external computing device, e.g., smartphone, laptop, desktop computer, etc. The test cartridge may further include a bar code or RFID tag which is read within the reader in order to assign an identity (e.g., name, or other identifier) to the test read. Accordingly, the reader 30 may further include a bar code reader or RFID reader which reads the bar code or RFID tag before or during the operation of reading the test device. The identifying indicia (name, employee number, etc.) is then associated with the test result and the combination of test result and identifying indicia can be transmitted to the external computing device, e.g., smart phone, using the wireless transmission capability of the reader, or optionally via the USB port on the rear of the reader (FIG. 17), or in some other manner. In one format, this data is in the form of a CSV file.

It may also be desirable to upload anonymized test results to a database, either locally on the remote computing device or in computing platform accessed over computer networks. In particular, the test results and optionally information regarding the subject having the test performed, such as age, sex, location, date/time, etc., but anonymized, is obtained from the reader or the reader in combination with a local computing device, e.g., smartphone, and transmitted to a web portal, or database. This process can occur in a distributed manner, for example over a large number of readers deployed in a geographic area, such as city, state or even country. The accumulation of such information in the database can be mined for many possible beneficial uses, for example to identify areas of high or low seroconversion rates.

Accordingly, in one possible configuration an app for a smartphone is provided which includes features for receiving the test results wirelessly from the reader 30 and additional user interface prompts or features to enter information regarding the subject taking the test (optionally, their name, age, sex, location, time/date, and/or employee number, etc.) and such information is then transmitted to a database for storage and possible mining.

As another possible configuration, the computing device (e.g., smartphone) communicating with the reader wirelessly includes a GPS unit and an app or software that appends geographic coordinate locations to the test results which are reported by the reader. The geographic coordinates are determined by the computing device's GPS functionality and indicate the location of the computing unit, but since the computing unit is local to the reader, the location information is essentially the location of the reader, and, by extension, the location (at least to an approximate degree) of the person supplying the sample to the test device. In this configuration, the reader outputs the results and ID information (from bar codes, RFID tag or other) associated with the person taking the test, and possibly other information such as peak data, error codes, etc. and this information is passed by WIFI/Bluetooth to the computing device, e.g., smartphone. Embedded software in the reader's microprocessor controller generates an output CSV file with this information. The computing device appends geographic coordinate data (such as latitude and longitude) to the CSV file, such as shown in FIG. 41.

Figure 30:
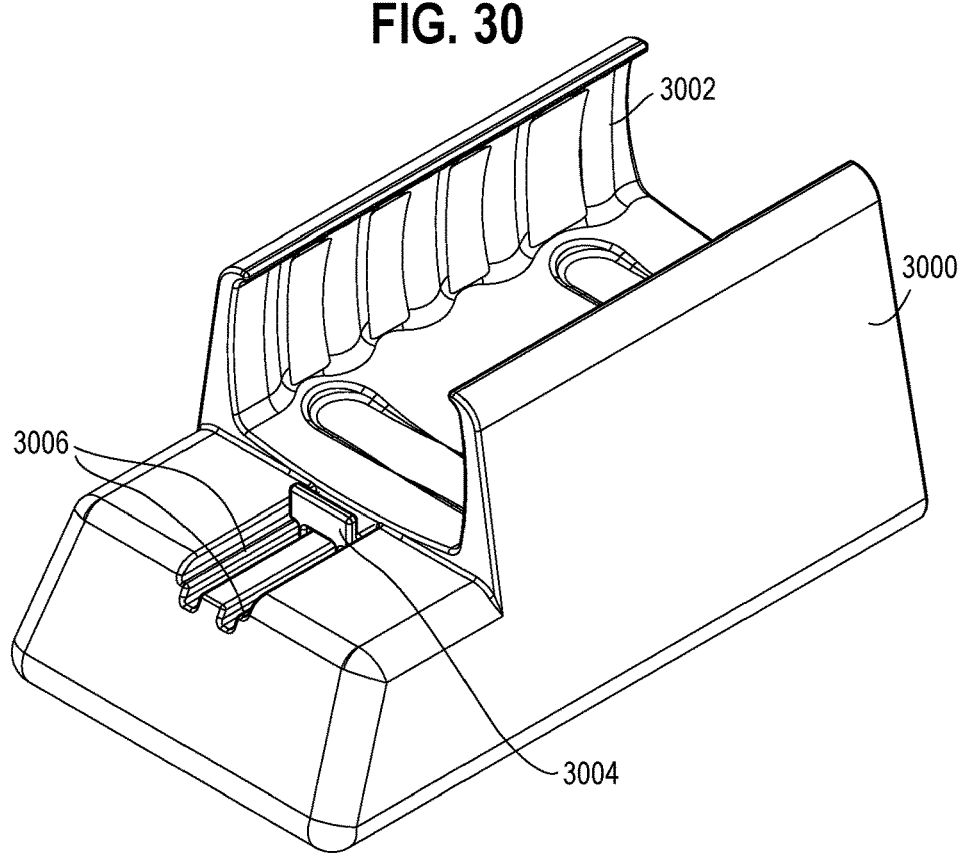
FIG. 30 is a perspective view of an accessory unit for the reader of FIG. 3 which includes an electro-mechanical system moving the tray into and out of the reader.

Alternatively, the GPS unit could be in the reader itself, or in the accessory unit of FIG. 30 and described later in this document.

The CSV-formatted data may then be imported into any convenient local data management application such as a spreadsheet or relational database, see FIG. 42, or uploaded to a cloud-based portal in an anonymized format, where it may be aggregated with the data obtained from a multitude of other readers, potentially hundreds or even thousands of readers. The aggregated cloud-based data can then be data mined, visualized, summarized or otherwise manipulated and presented to generate reports, for example to spot trends in seroconversion rates or show how seroconversion rates or test administration rates are trending in particular geographic areas or among different demographic groups of subjects.

Figure 43:
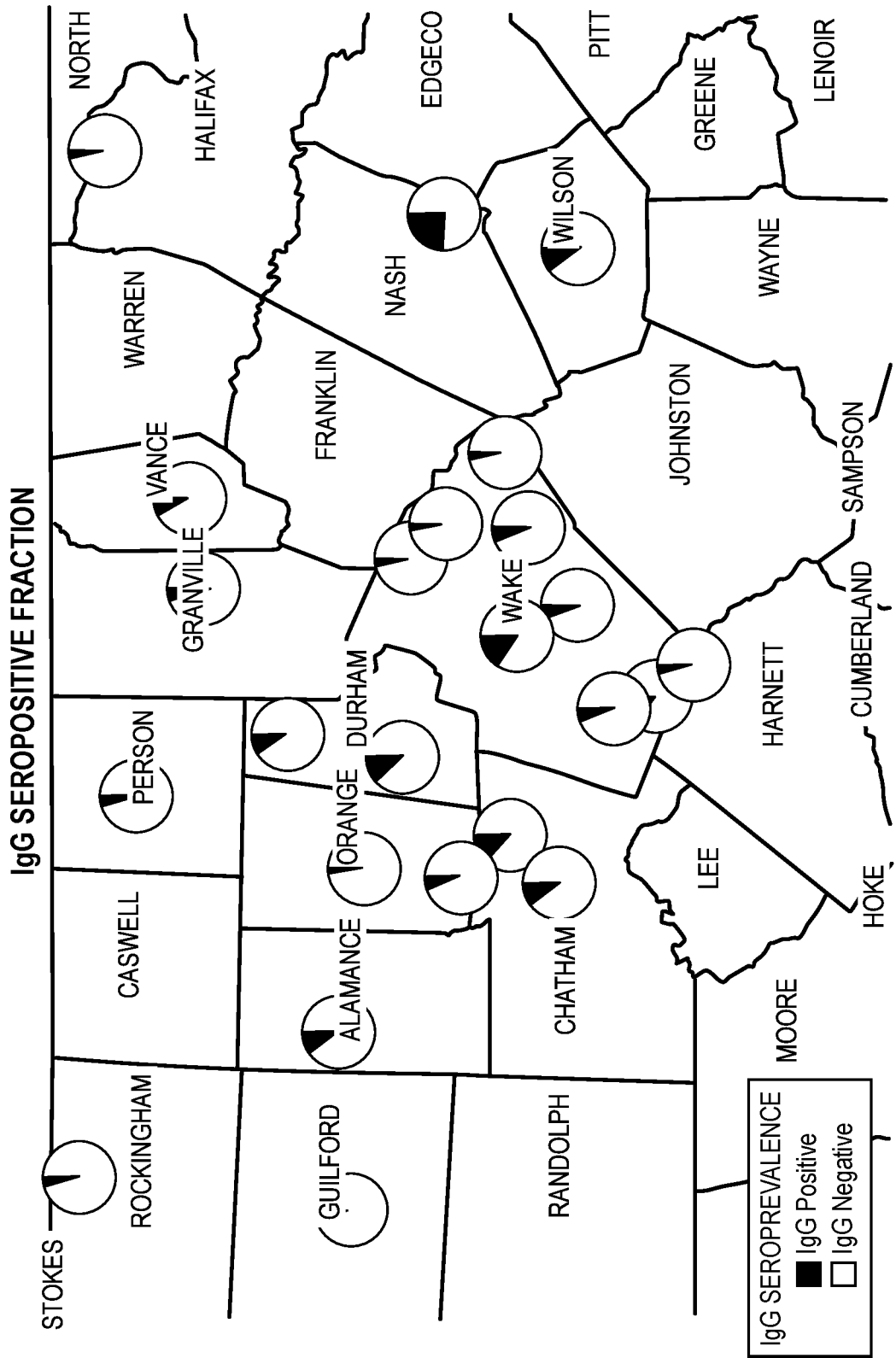
FIG. 43 is an illustration of a map showing the geographic distribution of epidemiological information based on the information in the database of FIG. 42.

Because this epidemiological information includes geographic coordinate information, it may be visualized by being overlaid on a map to visually display geographic differences in the summarized data. Such overlays may include heat maps or choropleth maps (both of which use color coding to indicate numeric differences over geographical areas), or a collection of graphs overlaying a map. One possible example is shown in FIG. 43. This map overlays pie charts centered on each reader's geographic location to represent the frequency of positive test results by region (in this example, cities and/or counties).

J. Accessory Device with Programmable Movement and Repeated Reading of Test Strip In another possible configuration, an accessory device (see FIGS. 30-38 and the description below) is provided which is used in conjunction with the reader and cartridge of FIG. 3. The accessory device 3000 (FIG. 30) is designed to hold the reader 30 (FIG. 31-32B) and provide an electromechanical means or system for moving the tray 32 in and out of the reader in a programmed fashion to enable repeated readings of the test cartridge over time. This means for moving the tray can take the form of a threaded rod 3302 (FIG. 33) or lead screw, which is activated by a motor 3300 in the accessory device, and a pull 3304 or other device connected to the threaded rod 3302. The pull 3304 engages mechanically with the tray to move it back and forth. Other suitable arrangements that function as described below can of course be devised.

Whereas in the embodiment of FIG. 3 the tray 32 and test cartridge 20 is moved into the reader manually and a result is obtained virtually instantly (e.g., in a few seconds), this accessory device configuration is designed for controlled, repeated reading of the entire exposed region of the test strip, or portions thereof, for seconds or possibly one or more minutes. The changes over time in the photodiode's detected decrease in test stripes' reflectance correlates to the gradual changes in intensity of the color change from lighter to deeper shades of red on the test strip. This embodiment further enables monitoring and recording the elapsed time for emergence of a positive result on the test strip (i.e., a peak which meets the necessary characteristics for a positive interpretation using the procedure of FIG. 9). This elapsed time data, possibly including further information as to the peak (e.g., height), slope of the photodiode response, and/or ratio of the test peak to the control line peak, can provide further information useful in assessing the state of the sample and, therefore, the result generated by the reader. For example and without limitation, lower titers of target antibody in the sample can give rise to more slowly-developing test stripe intensity, which can be detected by the photodiode output signal over time.

When a patient blood/buffer solution is applied to the sample cavity (22) in the cartridge 22 (FIG. 3), the sample progresses down the strip by capillary action. The leading edge of the sample, containing antigen-conjugated gold particles, moves further and engages the detection zone, e.g., IgG (or IgM) stripe, and these bind and are immobilized at the test stripe. Over time, the color grows more intense as more antigen-conjugated gold binds there. Thus, as presently understood, a higher titer (i.e., concentration) of the antibodies of interest (e.g., COVID-19 antibodies, for sake of example) will lead to faster emergence (and ultimately saturation) of the color in the IgG test line. In this accessory embodiment, the movement of the cartridge is controlled by the threaded rod and associated motor such that the photodiode detector in the optics unit of the reader is positioned to read that IgG test line area repeatedly over time, e.g. over a period of 1 to 60 seconds, or potentially longer (the time depending on many factors such as the test at issue). The movement of the tray may be paused or stopped entirely during the reading of the test line. The measurements of the change in photodiode output, slope, final peak height, etc., as a function of elapsed time, may be useful to characterize the titer of the patient's antibodies. In one configuration, the optics unit of the reader is configured to repeatedly scan the full test strip. Alternatively, the means for moving the tray then advances the tray and test cartridge further into the reader and the photodiode detector then reads the IgM test line, optionally over time as just stated as well, and then the Control line to record its color intensity, which will lead to an adjustment of the final reading results for the IgG and IgM test line.

The movement of the cartridge relative to the optics unit and photodiode may be programmed such that movement is stopped and the test line read repeatedly in the sequence at which the sample moves down the test strip and contacts the test lines in order (the one closest to the sample well being contacted first). It may be important, at least for some tests, that the reading of the test lines captures the initial ramp up, slope and asymptotic leveling off of the peak intensity as the color change occurs in the test line over time, and that the cartridge be moved to the second test line in the sequence in time to record that ramp up, slope and asymptotic levelling as well. These concerns would be obviated if the optics unit of the reader is configured with a light source and reading unit that captures the reflectance of all the test stripes without necessarily having to move the test strip, such as by use of a 2D imaging device or an array of photodiodes.

As an alternative it could be possible to place two optics units within the reader, one for the IgM line and one for the IgG line, so that both the IgM and IgG lines are read independently and simultaneously by the optics units over some period of time. Thus, measurements of the change in photodiode output, slope, final peak height, etc., as a function of time, are made for both lines independently and simultaneously, and that information can be processed within the reader to either generate a test result (e.g., "positive") or to characterize the result, e.g., "high positive", "low positive" or potentially "indeterminate."

In this embodiment a QR code can be placed on the bottom surface of the cartridge 20, which is read by the accessory device.

Figure 31:
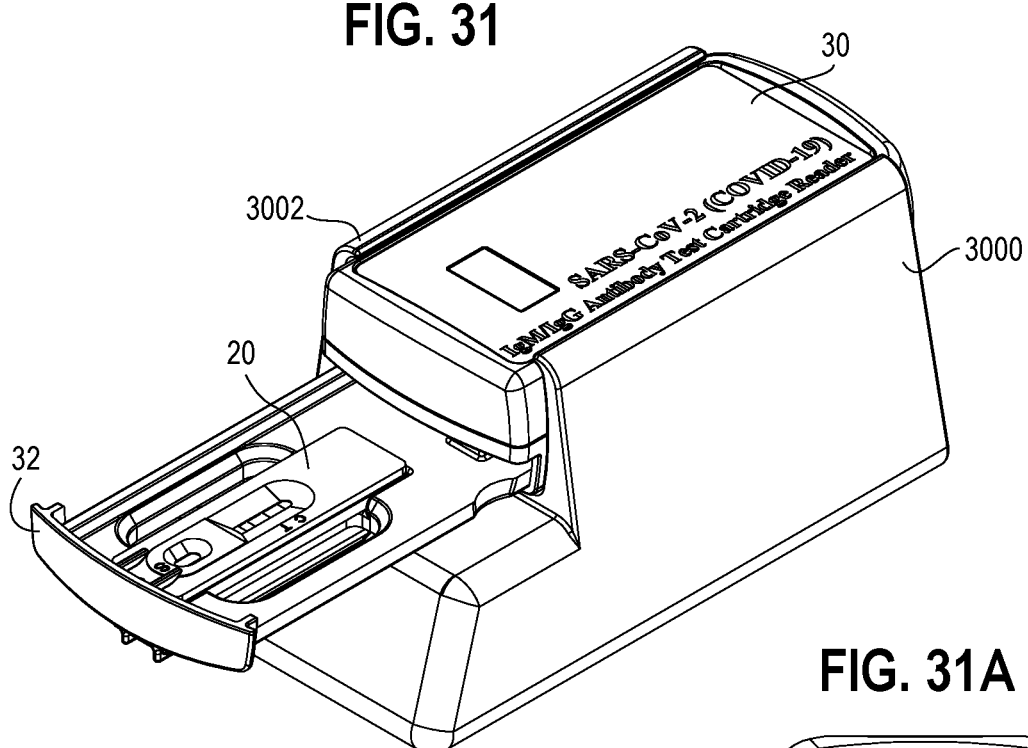
FIG. 31 is a perspective view of the accessory unit for the reader holding the reader, with the tray in the extended position with the test cartridge loaded in the tray.
Figure 31A:
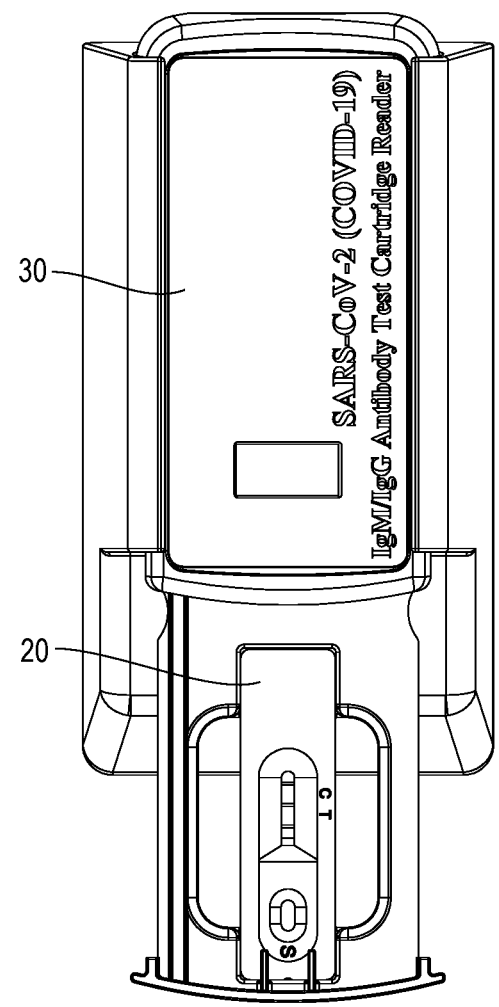
FIG. 31A is a top view of the reader, tray and test cartridge in the position shown in FIG. 31.
Figure 32:
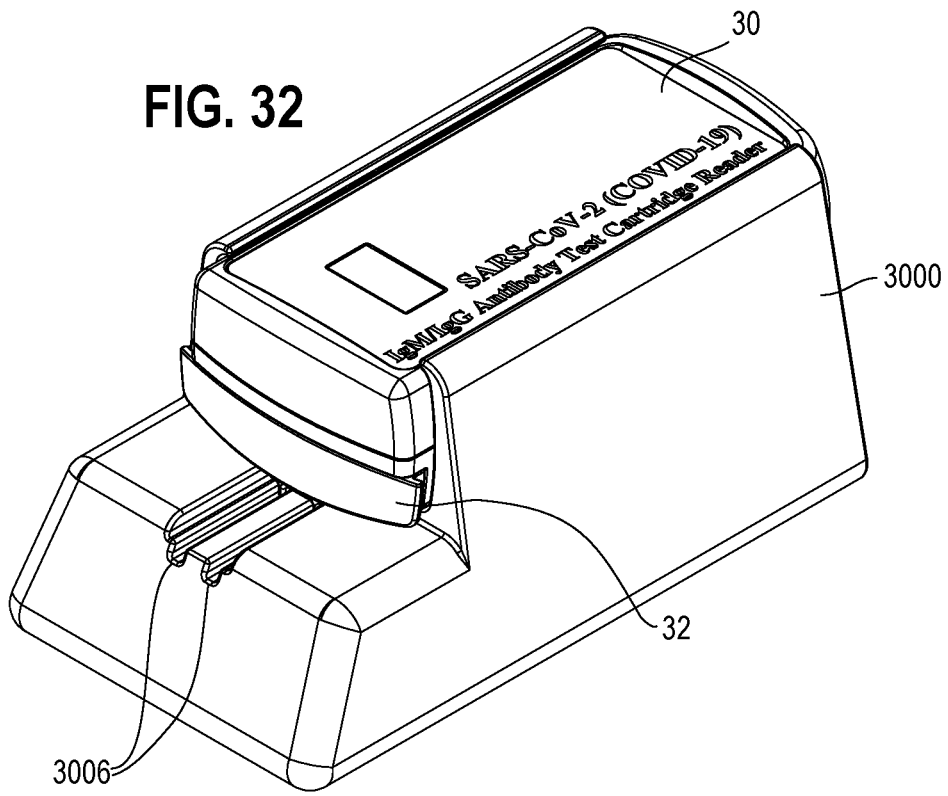
FIG. 32 is a perspective view of the accessory unit for the reader with the tray in the closed position for reading of the test cartridge.
Figure 32A:
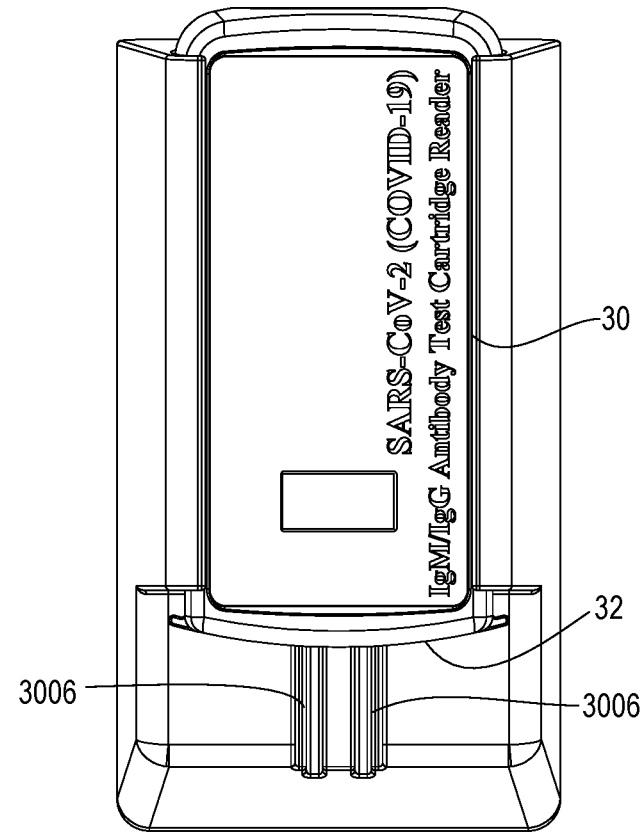
FIG. 32A is a top view of the reader and tray in the position shown in FIG. 32.
Figure 32B:
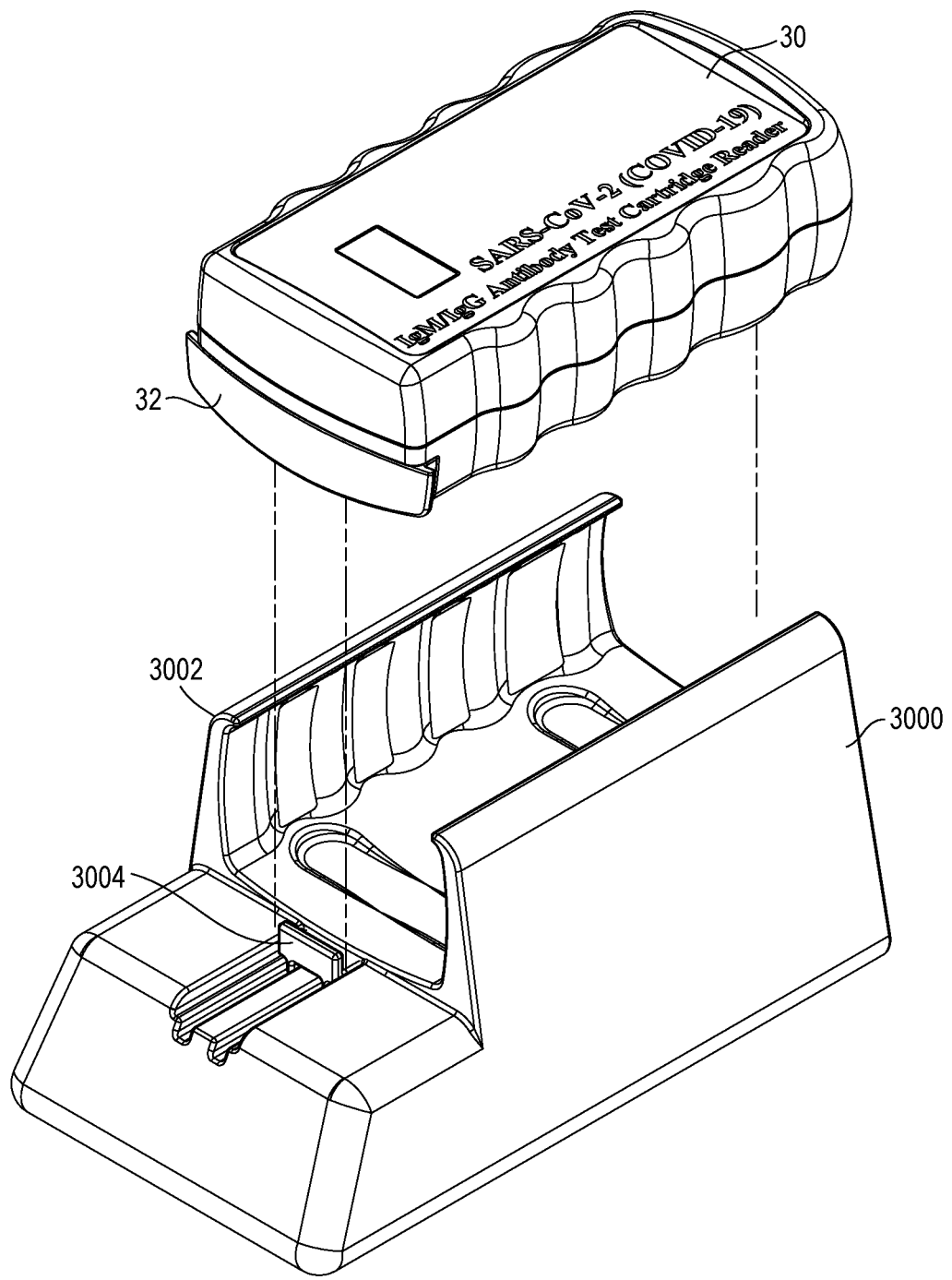
FIG. 32B is a perspective view of the reader and accessory unit of FIG. 32.

Referring now to FIGS. 30-38, the accessory device 3000 includes a cradle 3002 securely holding the reader 20. A drawer pull 3004 is connected to the threaded rod, which slides relative to the cradle in slots 3006. The pull 3004 engages mechanically with the tray (see FIG. 37) and guides the tray in and out of the reader. FIGS. 31 and 31A shows the accessory 3000 with the reader 30 held in the cradle 3002 and the motor energized to extend the pull 3004 to a fully extended position in which the test device 20 is loaded into the tray 32. FIGS. 32 and 32A shows the configuration where the motor is energized to insert the tray 32 into the reader 30, e.g. during reading. FIG. 32B shows how the fits into the accessory unit by expanding slightly the cradle 3002 to allow it to snugly fit in place as show in FIGS. 31 and 32.

Figure 33:
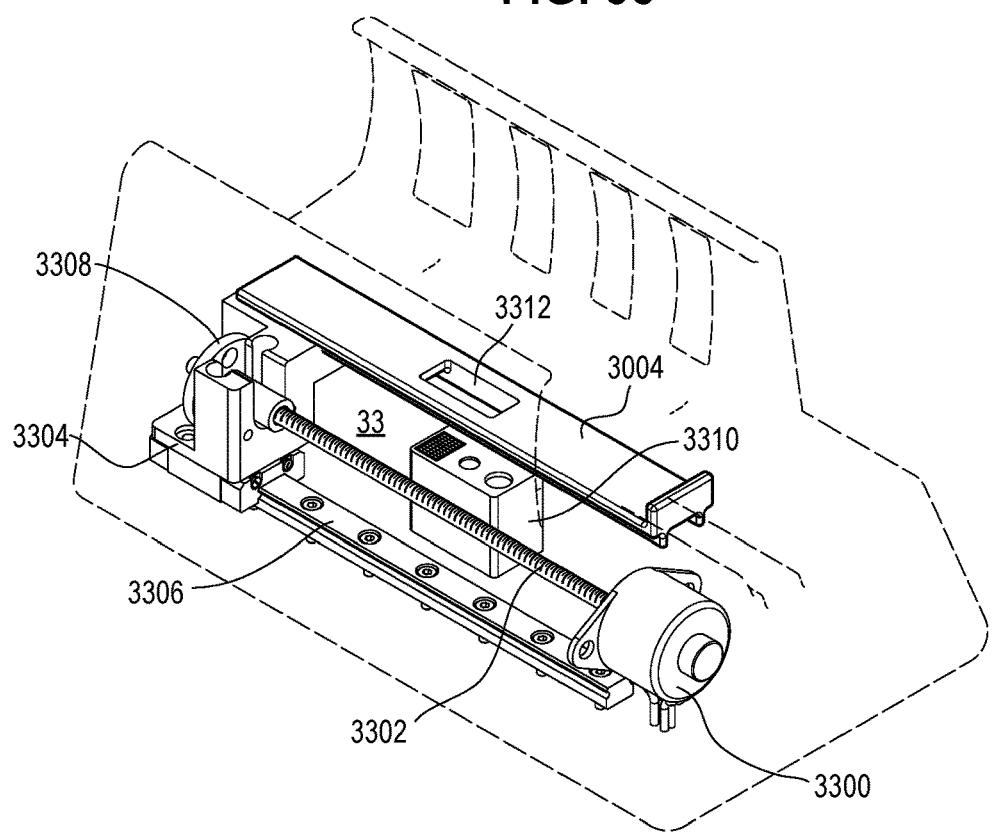
FIG. 33 is a perspective view of the electro-mechanical system designed to move the tray relative to the reader optics in a programmed manner, with the skin or housing for the accessory unit shown in dashed lines.

FIG. 33 is a perspective view of the electro-mechanical components in more detail, such components being located in with the accessory unit per se. The pull 3004 is mounted to a fixture 3304 which slides on a rail 3306. The motor 3300 rotates the threaded rod 3302 which causes the collar 3308 mounted to the end of the rod to move towards or away from the motor 3300, and thereby cause the pull 3004 to move between the positions shown in FIGS. 31 and 32.

The accessory includes a QR code reader 3310 which reads a QR code 3502 on the bottom surface of the test device 20. The aperture 3312 in the pull enables the reader 3310 to read the code as the drawer and test device are moved into the reader.

Figure 34:
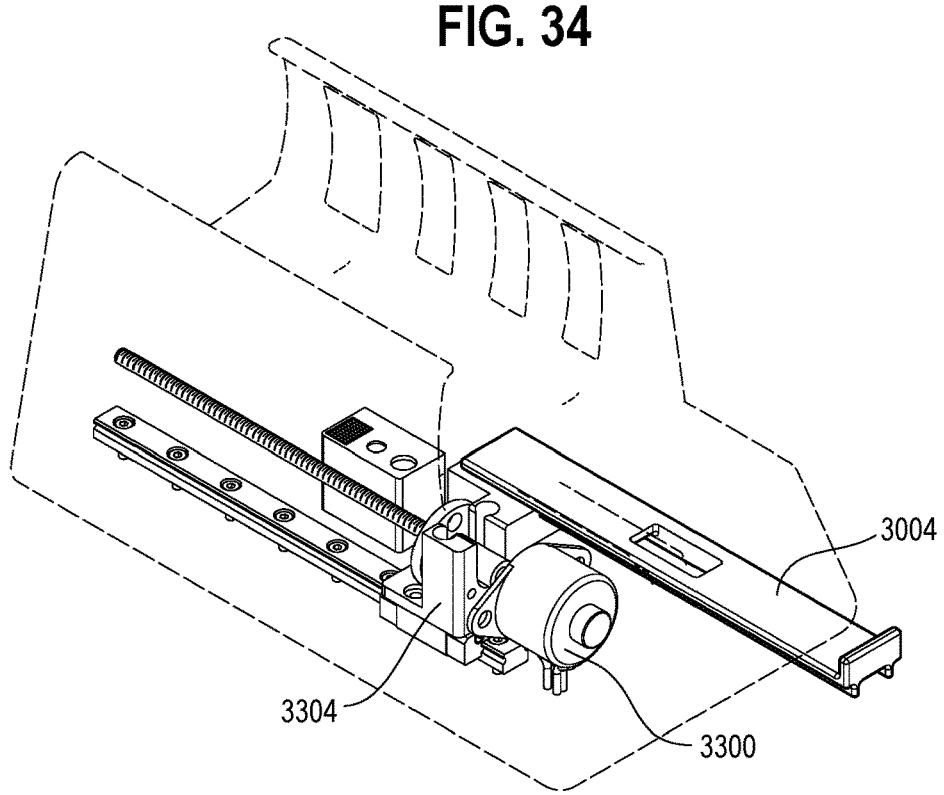
FIG. 34 is a perspective view of the electro-mechanical system of FIG. 33 with the pull extended.
Figure 34A:
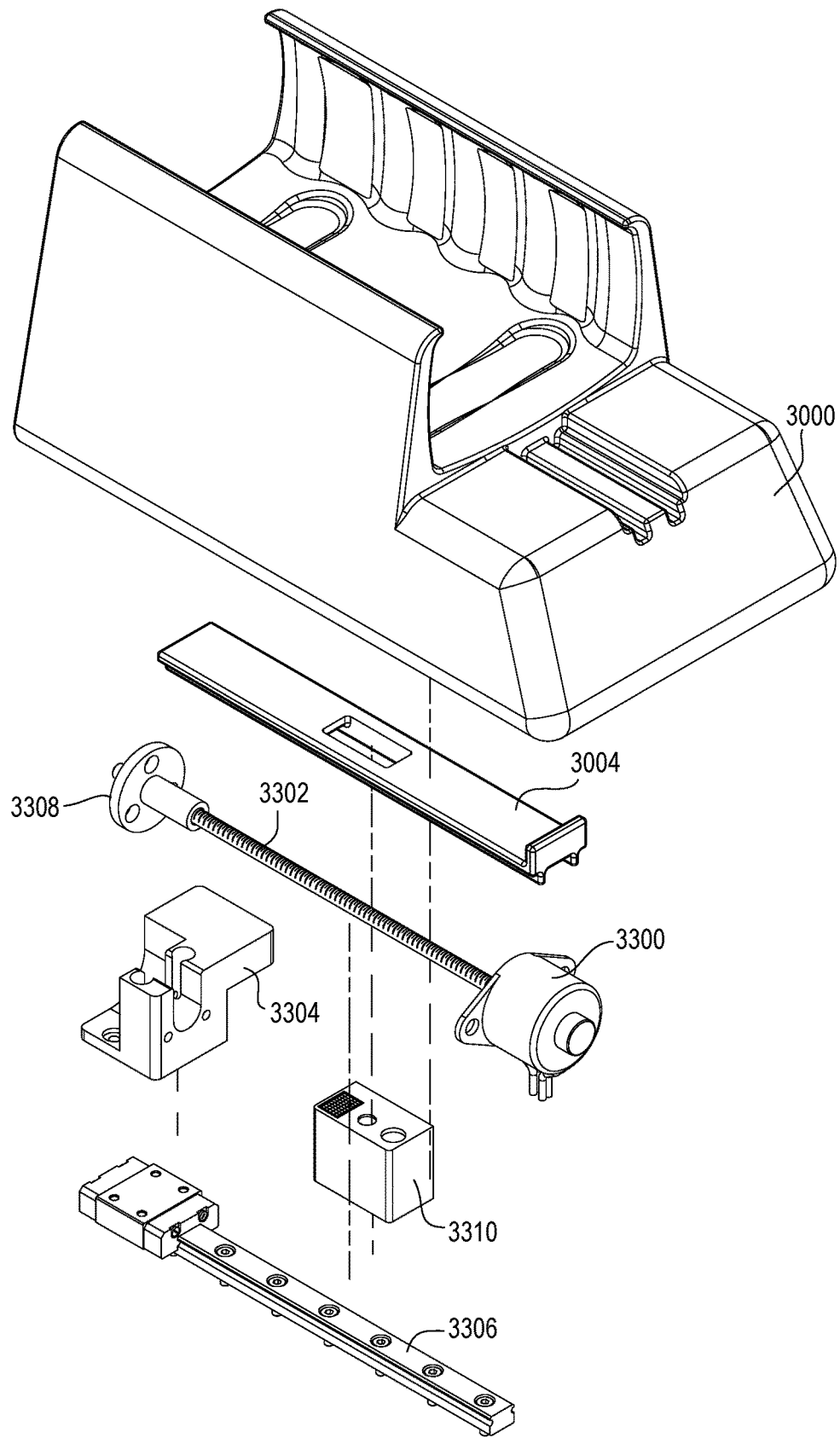
FIG. 34A is an exploded view of the electro-mechanical system of FIGS. 33 and 34.
Figure 38:
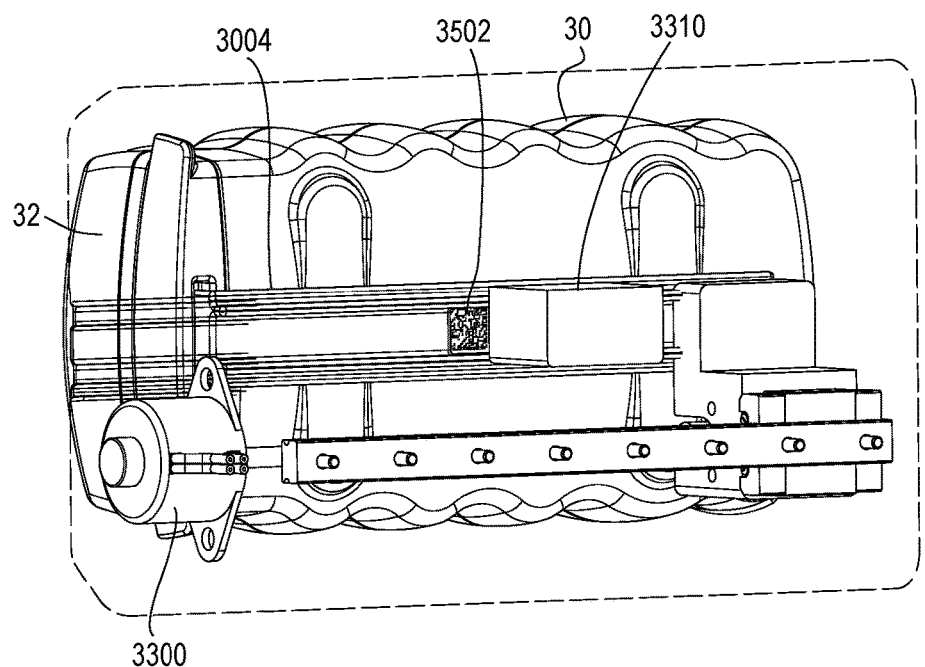
FIG. 38 is a view of the accessory unit from below, showing the electro-mechanical system moving the tray to the closed position.

FIG. 34 shows the motor 3300 energized to move the pull 3004 to the extended position, as in FIG. 31. FIG. 33 shows the motor energized to move the pull 3004 to the closed position, as shown in FIG. 38. FIG. 34A is an exploded view of the electro-mechanical system and the accessory unit 3000.

Figure 35:
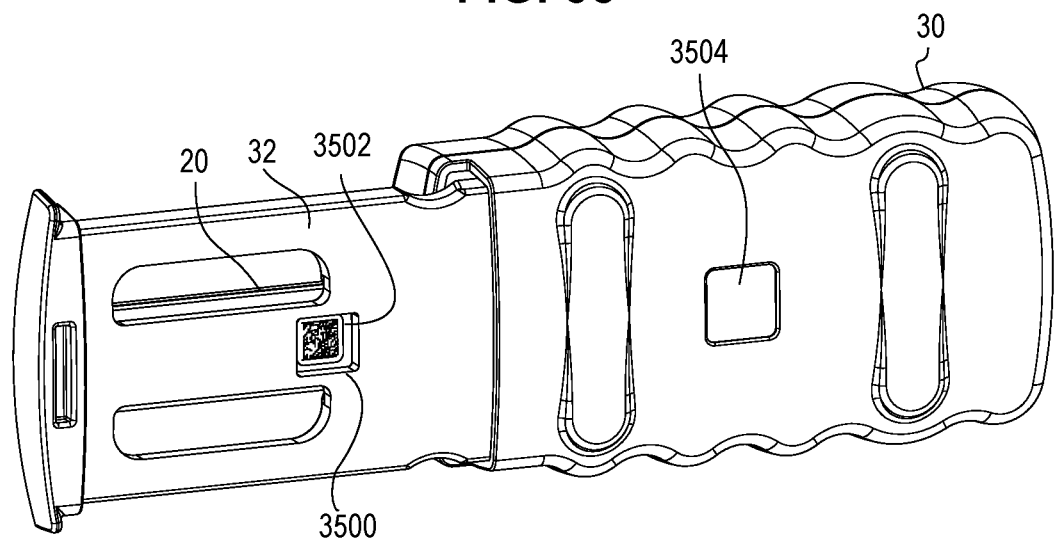
FIG. 35 is a bottom perspective view of the reader with the tray extended and showing a QR code on the test device visible through an aperture in the tray.
Figure 36:
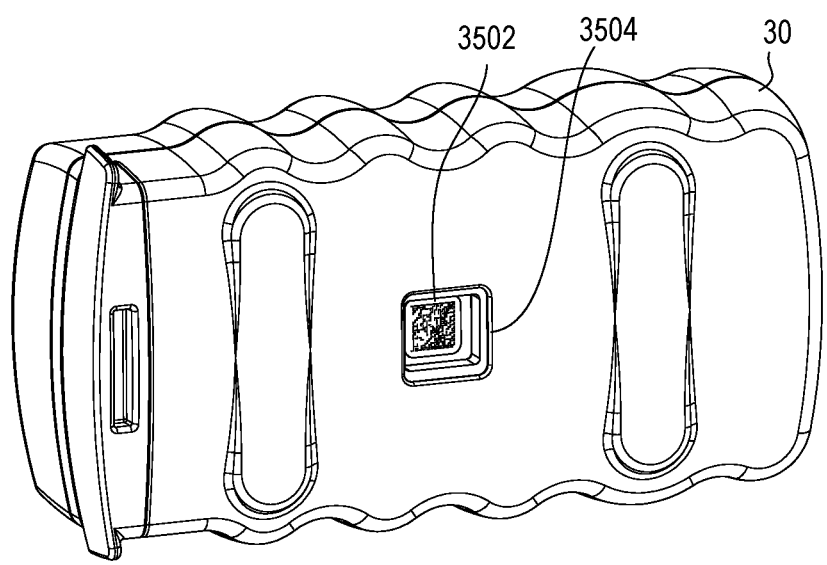
FIG. 36 is bottom perspective view of the reader with the tray closed.

FIG. 35 shows the QR code 3502 on the bottom surface of the test strip within the cartridge 20. The tray 32 includes an aperture 3500 which reveals the QR code when the cartridge is placed in the tray. The bottom of the reader 30 includes an aperture 3504 which reveals the QR code 3502 when the tray is fully inserted so that it can be read by the QR code reader 3310 (FIG. 33). See FIG. 36.

Figure 37:
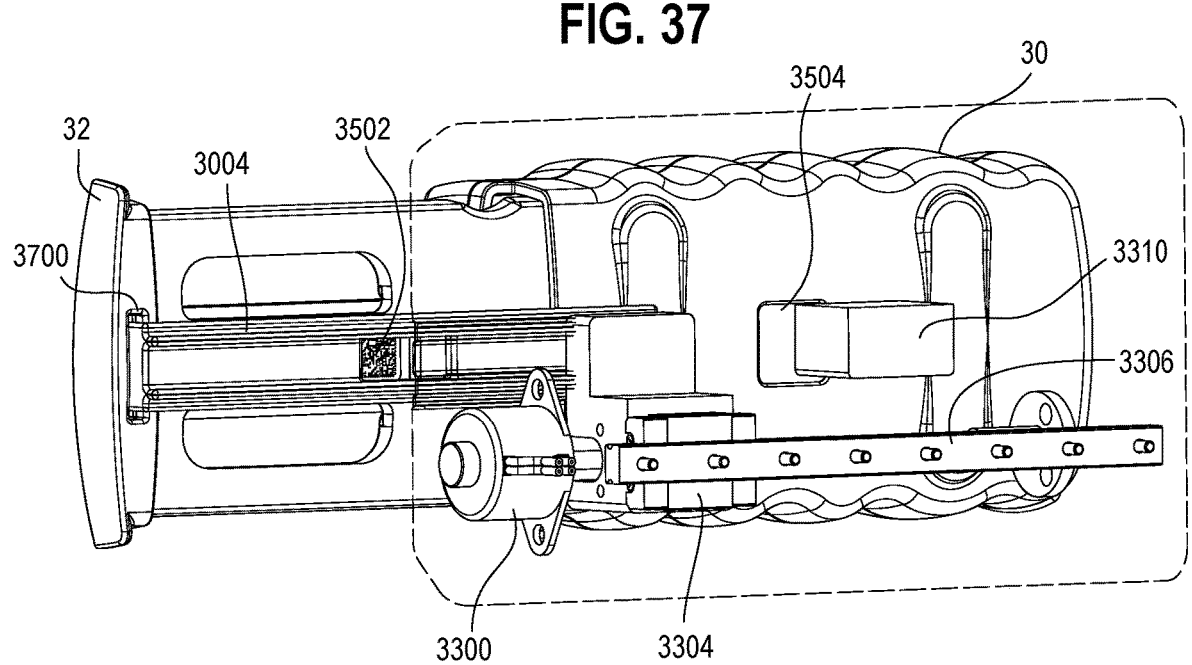
FIG. 37 is a view of the accessory unit from below, showing the engagement of the pull component of the electro-mechanical system engaging the tray.

FIG. 37 is a perspective view of the electro-mechanical system and reader and tray from below, with the tray in the extended position, showing a slot 3700 in the end of the tray in which the pull 3004 fits in order to engage the tray and allow it to be slid back and forth along the rail 3306.

FIG. 38 is a perspective view of the electro-mechanical system and reader and tray from below, with the tray moved to the closed or reading position, showing the QR reader 3310 in position to read the QR code 3502 placed on the bottom of the test device.

In one specific embodiment, an accessory unit 3000 to a lateral flow assay reader 30 having a moveable tray 32 holding a test device 20 has been described. The tray is moveable from open and closed positions (FIGS. 37, 38). The accessory unit 3000 includes a structure holding the reader, e.g., the cradle of FIG. 30, and an electro-mechanical system (3300, 3302, 3304, 3004) engaging the tray 32 and moving the tray and test device into the reader between the open and closed positions in a programmed manner (see FIGS. 37, 38), such that the test device is positioned proximate to the optics unit 1028 in the reader (FIG. 10) such that at least one of the one or more test lines is read continuously for a period of time by the optics unit, whereby the reader is able to record changes in the color intensity of the one or more test lines over time. In one possible embodiment, the reader is as shown in FIGS. 10 and 4 and discussed previously; however variations from that configuration are possible.

In one possible embodiment, the test device include at least two test lines (FIG. 3), and the programmable movement moves the tray such that the movement is stopped when both test lines are positioned proximate to the optics unit enabling the at least two test lines to be read continuously for a period of time by the optics unit. Optionally, the optics unit includes a photodiode reading the at least one test lines and a memory storing photodiode output as a function of time while the movement of the tray is in stopped condition. As shown in FIGS. 33 and 38, the accessory unit 3000 includes a QR code reader 3310.

The energizing of the motor 3300 and thus movement of the tray+cartridge into the reader is programmably controlled by a suitable processor in the accessory unit 3000 and program code for the motor written to accomplish the functions as described above. Thus, the accessory unit 3000 of FIGS. 30-38 includes a memory storing program code, one or more processors or microprocessors, a timer or clock, and additional electronics (power supply, etc.) to operate as described, and such details are of course within the ability of those skilled in the art of electro-mechanical systems. Optionally, the accessory unit includes a GPS unit.

Figure 39:
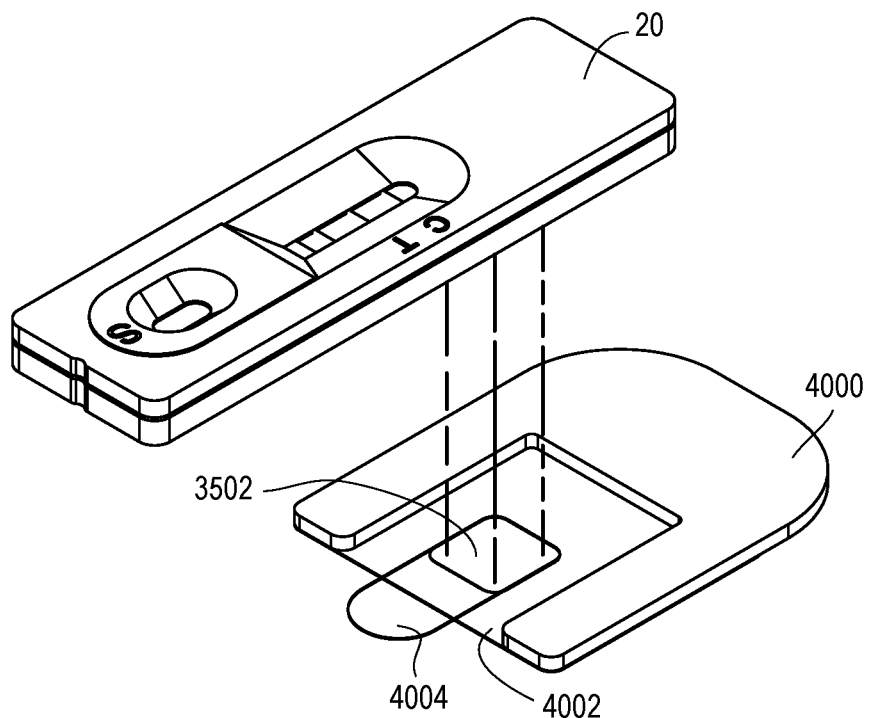
FIG. 39 is a perspective view of the test cartridge and a guide as seen from above; the guide aids in placement of a QR code on the bottom surface of the test cartridge.
Figure 40:
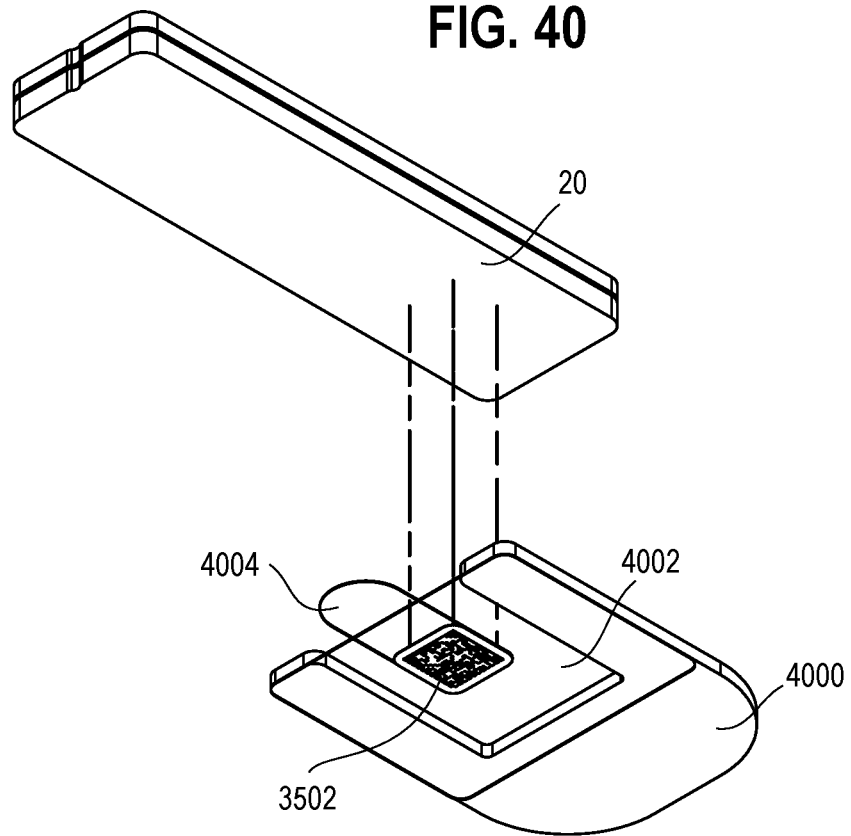
FIG. 40 is a perspective view of the test cartridge and guide of FIG. 39 as seen from below.
Figure 40A:
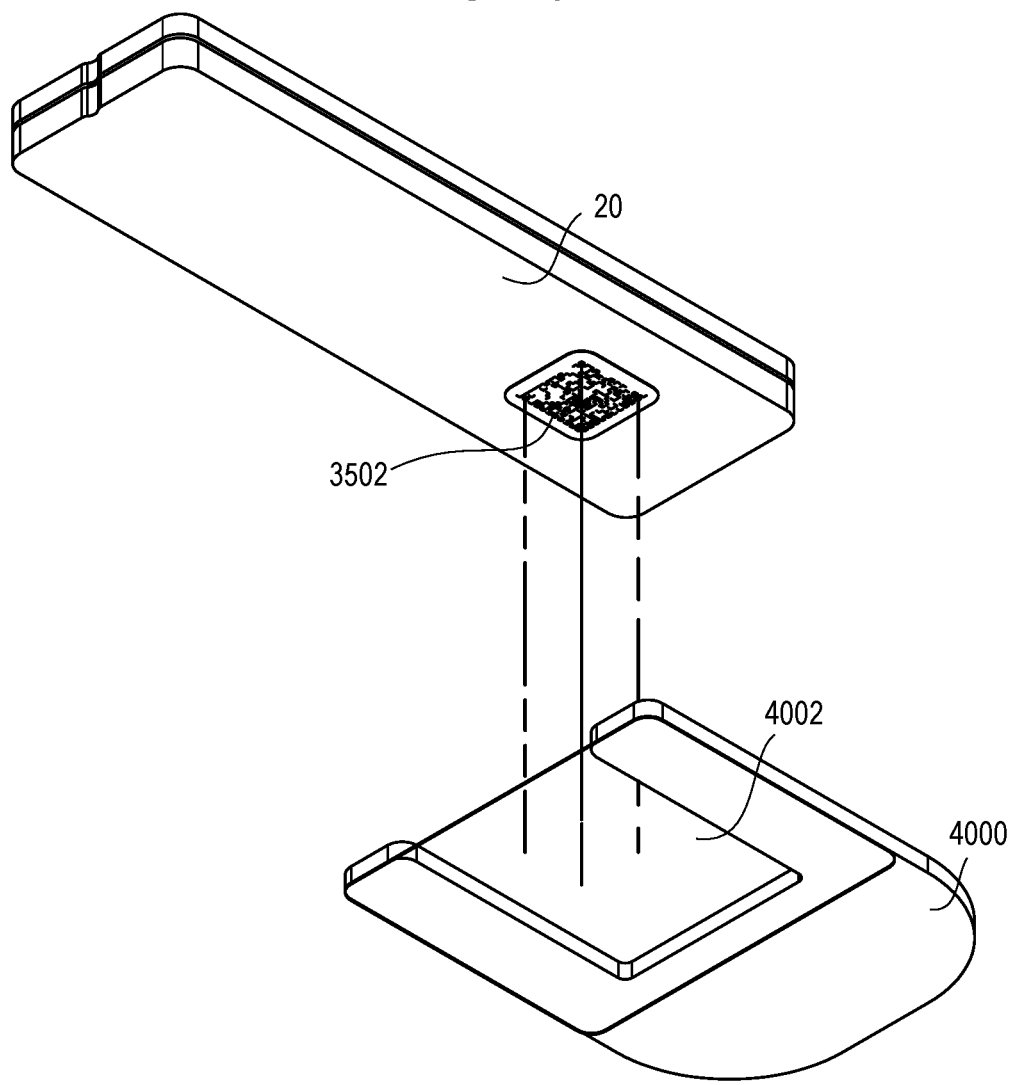
FIG. 40A is a perspective view of the test cartridge after the guide of FIGS. 38 and 39 has been used adhere the QR code to the bottom of the test cartridge.

Preferably, the QR code affixed to the bottom of the test device is positioned in a predetermined position, i.e., the location necessary such that it is exposed to the QR reader 3310 in the accessory unit when the tray is inserted for reading. The QR code can be applied to the test device at the time of use, by means of including the QR code as a portion of a sticker or cardstock item, with peel off adhesive or backing, to facilitate attachment of the sticker (and thus the QR code) in the correct location. For example, with reference to FIGS. 39 and 40, the sticker 4002 can include a guide 4000, or physical dimensions, such that the sides and one end of the sticker 4000 align with the sides and one end of the cartridge 20, thereby positioning the QR code 3502 the necessary distance (e.g., 1 inch) from the end of the cartridge 20 such that it appears in the window 3504 as shown in FIGS. 35 and 38. For example, the sticker 4002 has a width substantially equal to the width of the test device and the QR code 3502 is placed on the sticker a distance from one edge thereof (such as the end of the sticker) such that when the one end thereof is aligned with the end of the test device and the sticker affixed in this alignment position the QR code is in the predetermined position as shown in FIGS. 35 and 38. Examples of the guide 4000 are shown in the FIGS. 39 and 40. The portion 4004 of the sticker 4002 can have an adhesive backing, as well as the back side of the QR code, such that when the guide 4000 is removed the portion 4002 of the sticker also is removed only leaving the adhesive portion 4004 and the QR code 3502. FIG. 40A shows the QR code on the bottom the test cartridge after the guide has been used in the manner described.

Features and Advantages

The reader of this disclosure provides a number of advantages and features.

1. Ease of Use

The reader is designed to impose the least possible workflow burden on the test administrator or user. The user simply slides the test cartridge 20 into the portable, battery-powered reader 30 and then immediately removes it, to record an instant readout.

Optionally, results are recorded in an industry-standard CSV file format for simple Bluetooth upload to a spreadsheet, a corporate database, and/or, after anonymization, to a managed web portal, thus obviating the usual need for manual recordkeeping during test administration. Access to anonymized web portal data will also allow detailed data mining to monitor actual test cartridge and reader performance in the field and evaluate use patterns—analyses that should prove invaluable for everything from FDA approval to ex post facto quality assurance to new product development. It could also yield unparalleled and epidemiologically valuable insight into the evolution of the geographic distribution and spread of disease, e.g., COVID-19 seropositivity, in real time.

2. Reproducible Results.

The test reader's integrated optics and light source obviate the requirement for controlled lighting conditions in which to consistently read LFIA tests, producing consistent results in test environments ranging from the most dimly lit room to the brightest sun-drenched parking lot.

3. High Sensitivity and Accuracy.

Weak-positive LFIA results are notoriously difficult to read consistently ("is that a pale red line, or just a dim stain?"). The reader's signal-processing software accurately and sensitively identifies and quantifies weak-positive test lines and rejects random stains.

4. Eliminate Lot-to-Lot Test Variability.

A manufacturer of the disclosed reader 30 may largely at the mercy of the test device manufacturer's unknown quality control standards, which may or may not be up to regulatory expectations. The reader's ratiometric signal processing removes as much variance as possible by judging test results as the ratio of test line intensity to control line intensity on the same cartridge ($I_T/I_C$), helping to ensure consistent results even in the face of reasonably wide lot-to-lot test variability.

5. Rugged Reliability.

In one possible configuration, the reader has no moving parts, making it both rugged and simple to manufacture at low cost. It's simple yet sophisticated self-test feature obviates the usual need for factory calibration of each reader and enables the reader to automatically compensate for performance degradation over time, thus greatly extending its useful lifetime even when used in harsh environmental conditions.

6. Security Features Employers Want.

The reader may be configured with an RFID reader for corporate use, to automatically record each test subject's identity (via a no-touch read of the employee's RFID-enabled company ID badge), assuring that each test result is properly assigned to the correct employee by making record-keeping errors nearly impossible. In addition, this feature can provide a measure of fraud protection, making it difficult for a 'stand-in' to impersonate another employee (for example, an antibody-positive employee impersonating an antibody-negative friend).

While presently preferred embodiments are described with particularity, variation from the details thereof is possible within the scope of the present invention. The appended claims are offered by way of further descriptions of the disclosed subject matter.

We claim:

1. Apparatus configured for performing a test for presence of antibodies to the SARS-CoV-2 virus in a sample, comprising in combination:
    a lateral flow immunoassay test device including a strip having an axis and having a control line and two test lines oriented perpendicular to the axis, the two test lines changing color in the presence of IgG and IgM antibodies to the SARS-CoV-2 virus in the sample, respectively, the test device receiving the sample, and a reader for the lateral flow immunoassay testing device,
    wherein the reader comprises a housing enclosing electronics and an optics unit configured and positioned within the reader for reading the test lines and the control line of the test device;
    wherein the reader further comprises a tray extendable from the housing between a closed position and an open position,
    wherein the tray is adapted to receive the test device when the tray is extended to the open position, and
    wherein when the test device is placed in the tray and the tray moved to a closed position the test lines and control line are read by the optics unit; and
    wherein the tray further includes a surface, the surface provided with an optical calibration test pattern, the optical calibration test pattern comprising a linear series of bands of known, graded optical intensities spaced from the test device and positioned in alignment with the axis of the test device, and
    a processing unit using a reading of the optical calibration test pattern by the said optics unit to perform a self-test of the optics unit and correction for any nonlinearity of the electronics or optics unit, wherein the optical calibration test pattern and the test lines and the control line are read sequentially by the optics unit upon movement of the tray from the open position to the closed position,
    the processing unit further generating a result for the test device based on the reading of the test lines and control line by the optics unit indicating whether antibodies to the SARS-CoV-2 virus are present in the sample.

2. The apparatus of claim 1, further comprising a wireless transmitter transmitting results of reading the test device to a remote computing device.

3. The apparatus of claim 2, wherein the remote computing device is a smart phone.

4. The apparatus of claim 1, further comprising:
    an accessory unit to reader, the accessory unit comprising:
    a structure holding the reader, and
    an electro-mechanical system engaging the tray and moving the tray and test device into the reader between the open and closed positions in a programmed manner such that the test device is positioned proximate to the optics unit such that at least one of the test lines is read repeatedly for a period of time by the optics unit;
    whereby the reader is able to record changes in the color intensity of the one or more test lines over time.

5. The apparatus of claim 4, wherein the programmable movement moves the tray such that both test lines are positioned proximate to the optics unit enabling the at least two test lines to read repeatedly for a period of time by the optics unit.

6. The apparatus of claim 4, wherein the optics unit includes a photodiode reading the test lines and a memory storing photodiode output as a function of time while the movement of the tray is in a stopped condition.

7. The apparatus of claim 4, wherein the accessory unit further comprises a QR code reader.

8. The apparatus of claim 7, wherein the QR code reader is positioned within the accessory unit and oriented such that it can read a QR code provided on the test device when the test device is held in the accessory unit.

* * * * *